United States Patent
Ajellal et al.

(10) Patent No.: US 10,301,411 B2
(45) Date of Patent: May 28, 2019

(54) CATALYST SYSTEM FOR PRODUCING POLYETHYLENE COPOLYMERS IN A HIGH TEMPERATURE SOLUTION POLYMERIZATION PROCESS

(71) Applicant: BOREALIS AG, Vienna (AT)

(72) Inventors: Noureddine Ajellal, Helsinki (FI); Luigi Resconi, Ferrara (IT); Gerhard Hubner, Breitenaich (AT)

(73) Assignee: BOREALIS AG, Vienna (AT)

( * ) Notice: Subject to any disclaimer, the term of this patent is extended or adjusted under 35 U.S.C. 154(b) by 0 days.

(21) Appl. No.: 15/304,629

(22) PCT Filed: Apr. 15, 2015

(86) PCT No.: PCT/EP2015/058205
§ 371 (c)(1),
(2) Date: Oct. 17, 2016

(87) PCT Pub. No.: WO2015/158791
PCT Pub. Date: Oct. 22, 2015

(65) Prior Publication Data
US 2017/0037164 A1 Feb. 9, 2017

(30) Foreign Application Priority Data

Apr. 17, 2014 (EP) .................................. 14165143

(51) Int. Cl.
*C07F 17/00* (2006.01)
*C08F 4/6592* (2006.01)
(Continued)

(52) U.S. Cl.
CPC .............. *C08F 210/16* (2013.01); *C07C 2/34* (2013.01); *C07F 7/081* (2013.01); *C07F 7/12* (2013.01);
(Continued)

(58) Field of Classification Search
CPC .............. C08F 4/65927; C08F 4/65908; C08F 4/65912; C08F 210/16
See application file for complete search history.

(56) References Cited

U.S. PATENT DOCUMENTS 6,252,019 B1 * 6/2001 Ewen ....................... C08F 10/00
502/117
2014/0206819 A1 * 7/2014 Hafner .................. C07C 13/465
525/240

FOREIGN PATENT DOCUMENTS

EP 2532687 A2 12/2012
EP 2657285 A1 10/2013
(Continued)

OTHER PUBLICATIONS

International Search Report and Written Opinion issued in International Application No. PCT/EP2015/058204, dated Dec. 14, 2015.
International Search Report and Written Opinion issued in International Application No. PCT/EP2015/058205, dated Dec. 14, 2015.
Busico, et al. "Alk-1-ene polymerization in the presence of a monocyclopentadienyl Zirconium(IV) acetamidinate catalyst: Microstructural and mechanistic insights." Macromol. Rapid Commun, vol. 28, 2007, pp. 1128-1134.
Castignolles, et al., "Detection and quantification of branching in polyacrylates by size-exclusion chromatography (SEC) and melt-state 13C NMR spectroscopy." Polymer 50 (2009) 2373-83.
(Continued)

*Primary Examiner* — Caixia Lu
(74) *Attorney, Agent, or Firm* — Meunier Carlin & Curfman LLC

(57) ABSTRACT

Catalyst system for producing ethylene copolymers in a high temperature solution process, the catalyst system comprising (i) a metallocene complex of formula (I) wherein M is Hf X is a sigma ligand, L is a bridge of the formula $—SiR^8_2—$, wherein each $R^8$ is independently a $C_1$-$C_{20}$-hydrocarbyl, tri($C_1$-$C_{20}$-alkyl)silyl, $C_6$-$C_{20}$-aryl, $C_7$-$C_{20}$-arylalkyl or $C_7$-$C_{20}$-alkylaryl n is 0, 1 or 2 $R^1$ and $R^{1'}$ are the same or can be different and can be a linear or branched $C_1$-$C_6$-alkyl group, $R^2$ and $R^{2'}$ are the same or are different and are a $CH_2$—$R^9$ group, with $R^9$ being H or linear or branched $C_1$-$C_6$-alkyl group $R^5$ and $R^{5'}$ are the same or are different and can be H or a linear or branched $C_1$-$C_6$-alkyl group or a OR group, wherein R is a $C_1$-$C_6$-alkyl group $R^6$ and $R^{6'}$ are the same or are different and can be H or a $C(R^{10})_3$ group, with $R^{10}$ being the same or different and $R^{10}$ can be H or a linear or branched $C_1$-$C_6$-alkyl group or $R^5$ and $R^6$ and/or $R^{5'}$ and $R^{6'}$ taken together form an unsubstituted 4-7 membered ring condensed to the benzene ring of the indenyl moiety, and $R^7$ and $R^{7'}$ can be the same or are different and can be H or a linear or branched $C_1$-$C_6$-alkyl group (ii) an aluminoxane cocatalyst and/or (iii) a boron containing cocatalyst and (iv) optionally an aluminum alkyl compound.

18 Claims, No Drawings

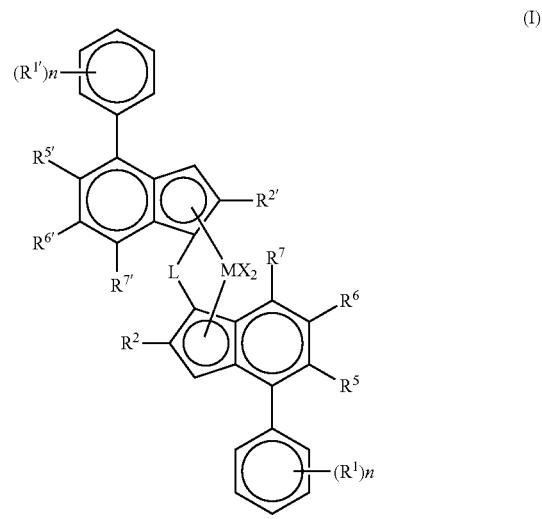

(51) Int. Cl.
  *C08F 210/18* (2006.01)
  *C08F 210/16* (2006.01)
  *C07F 7/12* (2006.01)
  *C07C 2/34* (2006.01)
  *C07F 7/08* (2006.01)
  *C08F 4/659* (2006.01)

(52) U.S. Cl.
  CPC .......... *C07F 17/00* (2013.01); *C08F 4/65927* (2013.01); *C07C 2531/14* (2013.01); *C07C 2531/38* (2013.01); *C08F 4/65908* (2013.01); *C08F 4/65912* (2013.01); *C08F 2500/03* (2013.01); *C08F 2500/11* (2013.01); *C08F 2500/12* (2013.01); *C08F 2500/18* (2013.01); *C08F 2800/20* (2013.01); *Y02P 20/52* (2015.11)

(56) References Cited

FOREIGN PATENT DOCUMENTS

| WO | 9714727 | A1 | 4/1997 |
|---|---|---|---|
| WO | 0009515 | A1 | 2/2000 |
| WO | 03049856 | A1 | 6/2003 |
| WO | 03051934 | A2 | 6/2003 |
| WO | 03102042 | A1 | 12/2003 |
| WO | 2006069733 | A1 | 7/2006 |
| WO | 2007116034 | A1 | 10/2007 |
| WO | 2007122098 | A1 | 11/2007 |
| WO | 2010052260 | A1 | 5/2010 |
| WO | 2010052263 | A1 | 5/2010 |
| WO | 2010052264 | A1 | 5/2010 |
| WO | 2011076780 | A1 | 6/2011 |
| WO | 2011135004 | A2 | 11/2011 |
| WO | 2011135005 | A2 | 11/2011 |
| WO | 2012001051 | A1 | 1/2012 |
| WO | 2012001052 | A2 | 1/2012 |
| WO | 2012075560 | A1 | 6/2012 |
| WO | 2012084961 | A1 | 6/2012 |
| WO | 2013007650 | A1 | 1/2013 |
| WO | WO 2013/007650 | * | 1/2013 |
| WO | 2015158791 | A2 | 10/2015 |

OTHER PUBLICATIONS

Chukanova, et al., "Polymerization of propylene using isospecific rac-Me2Si(2-Me,4-Phlnd)2ZrCl2 catalyst immobilized on polyethylene with grafted poly(acrylic acid)", Polymer science. Series A, Chemistry, physics 43.8 (2001): 787-792.

Ewen, et al., "Evaluation of the dimethylsilyl-bis(2-methyl-4-phenyl-1-indenyl) ligand with group 4 triad metals in propene polymerizations with methylaluminoxane", Macromolecular Rapid Communications vol. 19, Issue 1, Jan. 1998, pp. 71-73.

Filip, et al., "Heteronuclear decoupling under fast MAS by a rotor-synchronized Hahn-echo pulse train", Journal of Magnetic Resonance, vol. 176, Issue 2, Oct. 2005, pp. 239-243.

Griffin, et al., "Low-load rotor-synchronised Hahn-echo pulse train (RS-HEPT) 1H decoupling in solid-state NMR: factors affecting MAS spin-echo dephasing times.", Mag. Res. In Chem. 2007 45, S1, S198.

Hintermann, et al., "Expedient syntheses of the N-heterocyclic carbene precursor imidazolium salts IPr•HCI, IMes•HCI and IXy•HCl", Beilstein J. Org. Chem. 2007, 3, 1-5.

Klimke, et al., "Optimisation and Application of Polyolefin Branch Quantification by Melt-State 13C NMR Spectroscopy", Macromolecular Chemistry and Physics vol. 207, Issue 4, Feb. 24, 2006, 382-395.

Liu, et al., "Poly(ethylene-co-1-octene) Characterization by High-Temperature Multidimensional NMR at 750 MHz", Macromolecules 2001, 34, 4757-4767.

Matsubara, et al., "Synthesis and Structures of Nickel Halide Complexes Bearing Mono- and Bis-coordinated N-Heterocyclic Carbene Ligands, Catalyzing Grignard Cross-Coupling Reactions", Organometallics, 2006, 25 (14), 3422-3427.

Parkinson, et al., "Effect of Branch Length on 13C NMR Relaxation Properties in Molten Poly[ethylene-co-(α-olefin)] Model Systems", Macromol. Chem. Phys. 2007, 208, 2128-2133.

Hubner, et al., "Application of Melt-State NMR Spectroscopy for Polyolefin Characterization in Industry," NMR Spectroscopy of Polymers: Innovative Strategies for Complex Macromolecules, Chapter 24, 401, 2011.

Pollard, "Observation of Chain Branching in Polyethylene in the Solid State and Melt via 13C NMR Spectroscopy and Melt NMR Relaxation Time Measurements", Macromolecules, 2004, 37 (3), pp. 813-825.

Qiu, et al., "Improved Peak Assignments for the 13C NMR Spectra of Poly(ethylene-co-1-octene)s", Macromolecules 2007, 40, 6879-6884.

Randall, A Review of High Resolution Liquid $^{13}$Carbon Nuclear Magnetic Resonance Characterizations of Ethyelene-Based Polymers. Macromol. Sci., Rev. Macromol. Chem. Phys. 1989, C29, 201-317.

Stork, et al., "The Stereochemistry of the SN2' Reaction. I. Preparation of Pure trans-6-Alkyl-2-cyclohexen-1-ols", J. Am. Chem. Soc. 1956, 78, 4604-4608.

Ushakova, et al., Ethylene polymerization and ethylene-1-hexene copolymerization over immobilized metallocene catalysts, Kinetics and Catalysis, Feb. 2012, vol. 53, Issue 1, 75-83.

Wang, et al., "Long Chain Branching in Ethylene Polymerization Using Binary Homogeneous Metallocene Catalyst System", Polymer Reaction Engineering, vol. 7, 1999—Issue 3, 327-346.

Zhou, et al., "A new decoupling method for accurate quantification of polyethylene copolymer composition and triad sequence distribution with 13C NMR." J Magn Reson., 2007, 187(2), 225-33.

Non-Final Office Action dated Jul. 20, 2017 in U.S. Appl. No. 15/304,638.

Final Office Action dated Mar. 9, 2018 in U.S. Appl. No. 15/304,638 (7 pages).

Notice of Allowance dated Aug. 8, 2018 in U.S. Appl. No. 15/304,638 (7 pages).

Supplemental Notice of Allowance dated Aug. 30, 2018 in U.S. Appl. No. 15/304,638 (3 pages).

* cited by examiner

CATALYST SYSTEM FOR PRODUCING POLYETHYLENE COPOLYMERS IN A HIGH TEMPERATURE SOLUTION POLYMERIZATION PROCESS

The present invention is related to a new catalysts system, which is able to produce polyethylene copolymers in a high temperature solution polymerization process. The catalyst systems comprise a combination of selected Hf-bisindenyl complexes, substituted at least in position 2 and 4 of both indenyls along with a cocatalyst comprising an aluminoxane cocatalyst and/or a boron based cocatalyst, optionally in the presence of an aluminium alkyl compound. This combination remarkably gives rise to catalyst systems with excellent stability and allows production of polyethylene copolymers with increased comonomer incorporation.

Metallocene catalysts have been used to manufacture polyolefins for many years. Countless academic and patent publications describe the use of these catalysts in olefin polymerization. Metallocenes are now used industrially and polyethylenes and in particular polypropylenes are often produced using cyclopentadienyl based catalyst systems with different substitution patterns.

Several of these metallocene catalysts have been described for the use in solution polymerization in particular for producing polypropylene.

For example WO 2007/116034 describes i.a. a catalyst system comprising racemic dimethylsilylbis(2-methyl-4-phenyl-5-methoxy-6-tert-butylinden-1-yl)dichlorozirconium and methylalumoxane cocatalyst for producing polypropylene in a solution polymerization process at temperatures between 100° C. and 120° C.

It is mentioned that the metallocene compounds can also be used for preparing ethylene copolymers, preferably ethylene-butene copolymers, but it is said that such copolymers are obtained by using gas phase processes.

Also WO 2007/122098 describes the use of the complex racemic dimethylsilylbis(2-methyl-4-(4-tert-butylphenyl)-1,5,6,7-tetrahydro-s-indacen-1-yl)dichlorozirconium in combination with an alumoxane cocatalyst for producing ethylene copolymers at 100° C.

WO 2011/135004 complexes as described in WO 2007/116034, like racemic dimethylsilylbis(2-methyl-4-phenyl-5-methoxy-6-tert-butylinden-1-yl)dichlorozirconium and prepared according to the emulsion/solidification method as described in WO 2003/051934 are disclosed. These complexes are activated with an alumoxane cocatalyst and used for WO 2012/075560 further describes a multi stage (at least two stage) solution polymerization process for preparing ethylene copolymers, wherein a phosphinimine catalyst is used with a cocatalyst comprising an alkylaluminoxane and an ionic activator, like a boron compound.

In none of the above cited literatures the problem of effective comonomer incorporation is mentioned.

However, for a process for producing ethylene copolymers to be efficient, it is important that the catalyst system used has a high reactivity for the C4-10 alpha-olefins used as comonomer.

Drawbacks arising from a low reactivity for the C4-10 alpha-olefin comonomer are e.g. increasing amounts of the alpha-olefin comonomer that are needed for introducing a certain amount of higher alpha-olefin comonomer units into the polymer and/or removal of non-reacted higher alpha-olefin from the polymer powder.

One further point to be noted is that high-temperature solution processes for olefin polymerization require a thermally robust catalyst.

As is discussed in WO 2003/102042 solution processes are characterized by short residence times. Consequently, in addition to having temperature stability, the catalyst systems used in these processes must activate quickly and thoroughly. This contrasts sharply with the requirements for catalysts used in slurry and gas-phase processes, where residence times are longer and catalyst lifetime is more important. Thus, a catalyst that is valuable for slurry and gas-phase processes might be a poor choice for use in a high-temperature solution process, and vice-versa. As solution to this problem WO 2003/102042 suggests to use organometallic complexes having Group 3-10 transition metal and a bridged indeno-indolyl ligand in combination with an activator, which is preferably methylalumoxane.

Although a lot of work has been done in the field of metallocene catalysts, there still remains a need to find new catalyst systems for ethylene copolymerization, which are able to produce polymers with desired properties and which have high reactivity for the used comonomers in order to achieve high comonomer incorporation and high thermal stability.

As a consequence, the inventors set out to develop a new catalyst system having superior polymerization behaviour than the above mentioned polymerization catalyst systems regarding to comonomer incorporation and thermal stability.

The present inventors have now found a new class of olefin polymerization catalyst systems, which are able to solve the problems disclosed above. In particular, the invention combines the use of special Hf-bisindenyl complexes with aluminoxane cocatalysts and/or a boron cocatalyst, optionally in the presence of an aluminium alkyl compound.

SUMMARY OF INVENTION

Thus, viewed from one aspect the invention relates to a catalyst system for producing ethylene copolymers in a high temperature solution process, the catalyst system comprising
(i) a metallocene complex of formula (I)

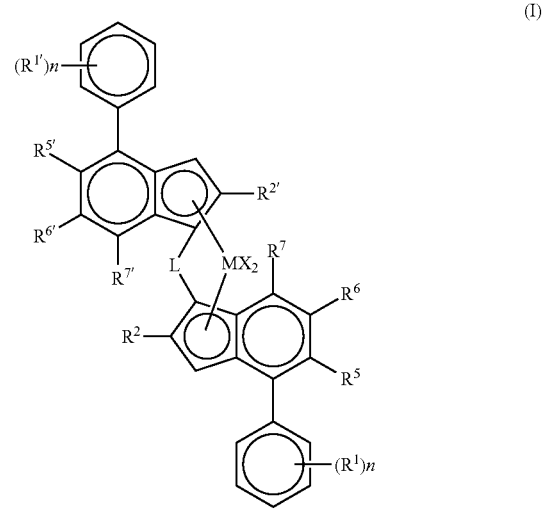

wherein
M is Hf
X is a sigma ligand
L is a bridge of the formula $-SiR^8_2-$, wherein each $R^8$ is independently a $C_1$-$C_{20}$-hydrocarbyl, tri($C_1$-$C_{20}$-alkyl)silyl, $C_6$-$C_{20}$-aryl, $C_7$-$C_{20}$-arylalkyl or $C_7$-$C_{20}$-alkylaryl,
n is 0, 1 or 2,
$R^1$ and $R^{1'}$ are the same or can be different and can be a linear or branched $C_1$-$C_6$-alkyl group, R² and R²' are the same or can be different and are a CH₂—R⁹ group, with R⁹ being H or linear or branched C₁-C₆-alkyl group R⁵ and R⁵' are the same or are different and can be H or a linear or branched C₁-C₆-alkyl group or a OR group, wherein R is a C₁-C₆-alkyl group R⁶ and R⁶' are the same or are different and can be H or a C(R¹⁰)₃ group, with R¹⁰ being the same or different and R¹⁰ can be H or a linear or branched C₁-C₆-alkyl group or R⁵ and R⁶ and/or R⁵' and R⁶' taken together form an unsubstituted 4-7 membered ring condensed to the benzene ring of the indenyl moiety, and R⁷ and R⁷' can be the same or are different and can be H or a linear or branched C₁-C₆-alkyl group (ii) an aluminoxane cocatalyst and/or (iii) a boron containing cocatalyst and (iv) optionally an aluminium alkyl compound.

Viewed from another aspect the invention provides a process for the preparation of an ethylene copolymer comprising polymerizing ethylene and a C₄₋₁₀ alpha-olefin comonomer in a high temperature solution process at a temperature greater than 100° C. in the presence of a catalyst comprising:

(i) a metallocene complex of formula (I) as defined above (ii) an aluminoxane cocatalyst and/or (iii) a boron containing cocatalyst and (iv) optionally an aluminium alkyl compound.

Viewed from a further aspect the invention provides an ethylene copolymer made by a process as hereinbefore defined.

DETAILED DESCRIPTION OF THE INVENTION

Metallocene Complex

The Hf-bisindenyl metallocene complex, especially the complexes defined by the formula (I) specified in the present invention, used for manufacture of the ethylene copolymer are symmetrical or asymmetrical. For asymmetrical complexes that means that the two indenyl ligands forming the metallocene complex are different, that is, each indenyl ligand bears a set of substituents that are either chemically different, or located in different positions with respect to the other indenyl ligand. More precisely, they are chiral, racemic bridged bisindenyl metallocene complexes.

Whilst the complexes of the invention may be in their syn configuration, ideally they are in their anti configuration. For the purpose of this invention, racemic-anti means that the two indenyl ligands are oriented in opposite directions with respect to the cyclopentadienyl-metal-cyclopentadienyl plane, while racemic-syn means that the two indenyl ligands are oriented in the same direction with respect to the cyclopentadienyl-metal-cyclopentadienyl plane, as shown in the Figure below.

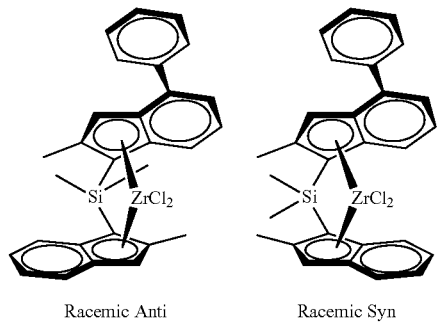

Racemic Anti          Racemic Syn

Formula (I) is intended to cover both syn and anti configurations.

By nature of their chemistry, both anti and syn enantiomer pairs are formed during the synthesis of the complexes. However, by using the ligands of this invention, separation of the preferred anti isomers from the syn isomers is straightforward.

It is preferred if the metallocene complexes of the invention are employed as the rac anti isomer. Ideally therefore at least 95% mol, such as at least 98% mol, especially at least 99% mol of the metallocene catalyst is in the racemic anti isomeric form.

The invention can be effected with a Hf-metallocene complex of formula (I)

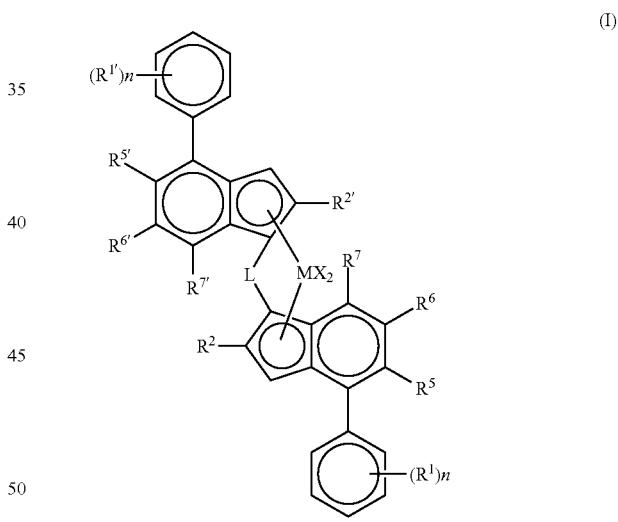

wherein

M is Hf

X is a sigma ligand

L is a bridge of the formula —SiR⁸₂—, wherein each R⁸ is independently a C₁-C₂₀-hydrocarbyl, tri(C₁-C₂₀-alkyl)silyl, C₆-C₂₀-aryl, C₇-C₂₀-arylalkyl or C₇-C₂₀-alkylaryl, n is 0, 1 or 2, R¹ and R¹' are the same or can be different and can be a linear or branched C₁-C₆-alkyl group, R² and R²' are the same or can be different and are a CH₂—R⁹ group, with R⁹ being H or linear or branched C₁-C₆-alkyl group $R^5$ and $R^{5'}$ are the same or are different and can be H or a linear or branched $C_1$-$C_6$-alkyl group or a OR group, wherein R is a $C_1$-$C_6$-alkyl group $R^6$ and $R^{6'}$ are the same or are different and can be H or a $C(R^{10})_3$ group, with $R^{10}$ being the same or different and $R^{10}$ can be H or a linear or branched $C_1$-$C_6$-alkyl group or $R^5$ and $R^6$ and/or $R^{5'}$ and $R^{6'}$ taken together form an unsubstituted 4-7 membered ring condensed to the benzene ring of the indenyl moiety, and $R^7$ and $R^{7'}$ can be the same or are different and can be H or a linear or branched $C_1$-$C_6$-alkyl group In the formula (I) each X, which may be the same or different, is a sigma ligand, preferably a hydrogen atom, a halogen atom, a $R^{11}$, $OR^{11}$, $OSO_2CF_3$, $OCOR^{11}$, $SR^{11}$, $NR^{11}_2$ or $PR^{11}_2$ group wherein $R^{11}$ is a linear or branched, cyclic or acyclic, $C_1$-$C_{20}$-alkyl, $C_2$-$C_{20}$-alkenyl, $C_2$-$C_{20}$-alkynyl, $C_6$-$C_{20}$-aryl, $C_7$-$C_{20}$-alkylaryl or $C_7$-$C_{20}$-arylalkyl radical; optionally containing heteroatoms belonging to groups 14-16 or is $SiR^{11}_3$, $SiHR^{11}_2$ or $SiH_2R^{11}$. $R^{11}$ is preferably a $C_{1-6}$-alkyl, phenyl or benzyl group, whereby the term halogen includes fluoro, chloro, bromo and iodo groups, preferably chloro groups.

More preferably each X is independently a hydrogen atom, a halogen atom, $C_{1-6}$-alkoxy group or an $R^{11}$ group, e.g. preferably a $C_{1-6}$-alkyl, phenyl or benzyl group.

Most preferably X is chlorine or a methyl radical. Preferably both X groups are the same.

$R^1$ and $R^{1'}$ are the same and are a linear or branched $C_1$-$C_6$-alkyl group, preferably a linear or branched $C_1$-$C_4$-alkyl group, more preferably a linear or branched butyl-group and most preferably $R^1$ and $R^{1'}$ are tert-butyl.

n is 0, 1 or 2, preferably 1 or 2,

If n is 1, then $R^1$ and $R^{1'}$ are preferably on position 4 (para) of the phenyl ring and if n is 2 then $R^1$ and $R^{1'}$ are preferably on positions 3 and 5 of the phenyl ring.

In a preferred embodiment at least one of the phenyl groups is substituted with at least one of $R^1$ or $R^{1'}$, $R^2$ and $R^{2'}$ are the same or can be different and are a $CH_2$—$R^9$ group, with $R^9$ being H or linear or branched $C_1$-$C_6$-alkyl group, like methyl, ethyl, n-propyl, i-propyl, n-butyl, i-butyl, sec-butyl and tert-butyl. Preferably $R^2$ and $R^{2'}$ are the same and are a $CH_2$—$R^9$ group, with $R^9$ being H or linear or branched $C_1$-$C_4$-alkyl group, more preferably $R^2$ and $R^{2'}$ are the same and are a $CH_2$—$R^9$ group, with $R^9$ being H or linear or branched $C_1$-$C_3$-alkyl group and most preferably $R^2$ and $R^{2'}$ are either both methyl or both i-butyl.

$R^5$ and $R^{5'}$ are the same or are different and can be a linear or branched $C_1$-$C_6$-alkyl group or a OR group, wherein R is a linear or branched $C_1$-$C_6$-alkyl group, and $R^6$ and $R^{6'}$ are the same or are different and can be H or a $C(R^{10})_3$ group, with $R^{10}$ being the same or different and $R^{10}$ can be H or a linear or branched $C_1$-$C_6$-alkyl group, or $R^5$ and $R^6$ and/or $R^{5'}$ and $R^{6'}$ taken together form an unsubstituted 4-7, preferably 5-6 membered ring condensed to the benzene ring of the indenyl moiety.

If one of $R^5$ and $R^6$ or $R^{5'}$ and $R^{6'}$ together form an unsubstituted 4-7, preferably 5-6 membered ring condensed to the benzene ring of the indenyl moiety, then the substituents on the other indenyl moiety (either $R^5$ and $R^6$ or $R^{5'}$ and $R^{6'}$) are preferably (for $R^5$ or $R^{5'}$) a OR group wherein R is a linear or branched $C_1$-$C_6$-alkyl group, like methyl, ethyl, n-propyl, i-propyl, n-butyl, i-butyl, sec-butyl and tert-butyl, preferably a linear $C_1$-$C_4$-alkyl group, more preferably a $C_1$-$C_2$-alkyl group and most preferably a $C_1$-alkyl group and (for $R^6$ or $R^{6'}$) a $C(R^{10})_3$ group, with $R^{10}$ being the same or different and $R^{10}$ can be H or a linear or branched $C_1$-$C_6$-alkyl group, preferably with $R^{10}$ being the same or different and $R^{10}$ being a linear or branched $C_1$-$C_4$-alkyl group, more preferably with $R^{10}$ being the same and $R^{10}$ being a $C_1$-$C_2$-alkyl group, most preferably the $C(R^{10})_3$ group is a tert-butyl group.

In one embodiment both of $R^5$ and $R^6$ as well as $R^{5'}$ and $R^{6'}$ together form an unsubstituted 4-7, preferably 5-6 membered ring condensed to the benzene ring of the indenyl moiety. More preferably both of $R^5$ and $R^6$ as well as $R^{5'}$ and $R^6R^5$ and $R^6$ or $R^{5'}$ and $R^{6'}$ form an unsubstituted 5 membered ring condensed to the benzene ring of the indenyl moiety.

It is also possible that at both ligands $R^5$ and $R^6$ as well as $R^{5'}$ and $R^{6'}$ are hydrogen. A further possibility is that only one of the ligands is unsubstituted in position 5 and 6.

$R^7$ and $R^{7'}$ can be the same or are different and can be H or a linear or branched $C_1$-$C_6$-alkyl group, preferably $R^7$ and $R^{7'}$ are the same or are different and can be H or a linear or branched $C_1$-$C_4$-alkyl group and more preferably $R^7$ and $R^{7'}$ are the same or are different and can be H or a $C_1$-$C_2$-alkyl group.

For preferred complexes $R^7$ and $R^{7'}$ are the same and are both H, or for a further class of preferred complexes one of $R^7$ or $R^{7'}$ is a linear or branched $C_1$-$C_6$-alkyl group, preferably a linear or branched $C_1$-$C_4$-alkyl group and more preferably a $C_1$-$C_2$-alkyl group and the other is H.

L is a bridge of the formula —$SiR^8_2$—, wherein each $R^8$ is independently a $C_1$-$C_{20}$-hydrocarbyl, tri($C_1$-$C_{20}$-alkyl) silyl, $C_6$-$C_{20}$-aryl, $C_7$-$C_{20}$-arylalkyl or $C_7$-$C_{20}$-alkylaryl.

The term $C_{1-20}$ hydrocarbyl group therefore includes $C_{1-20}$ alkyl, $C_{2-20}$ alkenyl, $C_{2-20}$ alkynyl, $C_{3-20}$ cycloalkyl, $C_{3-20}$ cycloalkenyl, $C_{6-20}$ aryl groups, $C_{7-20}$ alkylaryl groups or $C_{7-20}$ arylalkyl groups or of course mixtures of these groups such as cycloalkyl substituted by alkyl.

Unless otherwise stated, preferred $C_{1-20}$ hydrocarbyl groups are $C_{1-20}$ alkyl, $C_{4-20}$ cycloalkyl, $C_{5-20}$ cycloalkyl-alkyl groups, $C_{7-20}$ alkylaryl groups, $C_{7-20}$ arylalkyl groups or $C_{6-20}$ aryl groups. Preferably $R^8$ are the same and are a $C_1$-$C_{10}$-hydrocarbyl or $C_6$-$C_{10}$-aryl group, like methyl, ethyl, propyl, isopropyl, tertbutyl, isobutyl, $C_{5-6}$-cycloalkyl, cyclohexylmethyl, phenyl or benzyl, more preferably both $R^8$ are a $C_1$-$C_4$-hydrocarbyl or $C_6$-aryl group and most preferably both $R^8$ are a $C_1$-alkyl group.

Especially preferred complexes of formula (I) are racemic dimethylsilanediylbis[2-iso-butyl-4-(4-tert-butyl-phenyl)-5,6,7-trihydro-s-indacen-1-yl] hafnium dichloride or dimethyl, racemic-anti-dimethylsilanediyl[η$^5$-6-tert-butyl-4-(3,5-di-tert-butylphenyl)-5-methoxy-2-methylinden-1-yl][η$^5$-4-(3,5-di-tert-butylphenyl)-2-methyl-5,6,7-trihydro-s-indacen-1-yl] hafnium dichloride or dimethyl, dimethylsilanediylbis[2-methyl-4-(4'-tert-butylphenyl)-5,6,7-trihydro-s-indacen-1-yl] hafnium dichloride or dimethyl, dimethylsilanediylbis[2-methyl-4-(3,5-di-tert-butylphenyl)-5,6,7-trihydro-s-indacen-1-yl] hafnium dichloride or dimethyl, racemic dimethylsilyl[(2-methyl-4-phenyl-5-methoxy-6-tert-butylinden-1-yl)-(2-methyl-4-(4'-tertbutylphenyl)-inden-1-yl)] hafnium dichloride or dimethyl and racemic dimethylsilyl[(2-methyl-4-(3',5'-di-tert-butylphenyl)-7-methylinden-1-yl)-(2-methyl-4-(4-tert-butylphenyl)-inden-1-yl)] hafnium dichloride or dimethyl either in their syn or anti configuration.

For the purpose of this invention, the terms dimethylsilyl, dimethylsilanediyl and dimethylsililene are equivalent.

Synthesis

The ligands required to form the catalysts of the invention can be synthesised by any process and the skilled organic chemist would be able to devise various synthetic protocols for the manufacture of the necessary ligand materials. WO2007/116034 discloses the necessary chemistry and is herein incorporated by reference. Synthetic protocols can also generally be found in WO2002/02576, WO2011/135004, WO2012/084961, WO2012/001052 and WO2011/076780.

Cocatalyst

To form an active catalytic species it is normally necessary to employ a cocatalyst as is well known in the art. The present invention requires the use of an aluminoxane cocatalyst and/or an boron containing cocatalyst, optionally in the presence of an aluminium alkyl compound.

The aluminoxane cocatalyst can be one of formula (II):

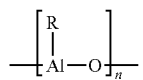
(II)

where n is usually from 6 to 20 and R has the meaning below.

Aluminoxanes are formed on partial hydrolysis of organoaluminum compounds, for example those of the formula $AlR_3$, $AlR_2Y$ and $Al_2R_3Y_3$ where R can be, for example, C1-C10 alkyl, preferably C1-C5 alkyl, or C3-10-cycloalkyl, C7-C12-arylalkyl or alkylaryl and/or phenyl or naphthyl, and where Y can be hydrogen, halogen, preferably chlorine or bromine, or C1-C10 alkoxy, preferably methoxy or ethoxy. The resulting oxygen-containing aluminoxanes are not in general pure compounds but mixtures of oligomers of the formula (I).

The preferred aluminoxane in the process according to the invention is methylaluminoxane (MAO). Since the aluminoxanes used according to the invention as cocatalysts are not, owing to their mode of preparation, pure compounds, the molarity of aluminoxane solutions hereinafter is based on their aluminium content.

Boron based cocatalysts of interest include boron compounds containing a borate $3^+$ ion, i.e. borate compounds. These compounds generally contain an anion of formula:

$(Z)_4B^-$ (III)

where Z is an optionally substituted phenyl derivative, said substituent being a halo$C_{1-6}$-alkyl or halo group. Preferred options are fluoro or trifluoromethyl. Most preferably, the phenyl group is perfluorinated.

Such ionic cocatalysts preferably contain a non-coordinating anion such as tetrakis(pentafluorophenyl)borate.

Suitable counterions are protonated amine or aniline derivatives or phosphonium ions. These may have the general formula (IV) or (V):

$NQ_4^+$ (IV) or $PQ_4^+$ (V)

where Q is independently H, $C_{1-6}$-alkyl, $C_{3-8}$ cycloalkyl, phenyl$C_{1-6}$-alkylene- or optionally substituted Ph. Optional substituents may be C1-6-alkyl, halo or nitro. There may be one or more than one such substituent. Preferred substituted Ph groups include therefore para-substituted phenyl, preferably tolyl or dimethylphenyl.

It is preferred if at least one Q group is H, thus preferred compounds are those of formula:

$NHQ_3^+$ (VI) or $PHQ_3^+$ (VII)

Preferred phenyl$C_{1-6}$-alkyl-groups include benzyl.

Suitable counterions therefore include: methylammonium, anilinium, dimethylammonium, diethylammonium, N-methylanilinium, diphenylammonium, N,N-dimethylanilinium, trimethylammonium, triethylammonium, tri-n-butylammonium, methyldiphenylammonium, p-bromo-N,N-dimethylanilinium or p-nitro-N,N-dimethylanilinium, especially dimethylammonium or N,N-dimethylanilinium. The use of pyridinium as an ion is a further option.

Phosphonium ions of interest include triphenylphosphonium, triethylphosphonium, diphenylphosphonium, tri(methylphenyl)phosphonium and tri(dimethylphenyl)phosphonium. A more preferred counterion is trityl ($CPh_3^+$) or analogues thereof in which the Ph group is functionalised to carry one or more alkyl groups. Highly preferred borates of use in the invention therefore comprise the tetrakis(pentafluorophenyl)borate ion.

Preferred ionic compounds which can be used according to the present invention include:
tributylammoniumtetra(pentafluorophenyl)borate,
tributylammoniumtetra(trifluoromethylphenyl)borate,
tributylammoniumtetra-(4-fluorophenyl)borate,
N,N-dimethylcyclohexylammoniumtetrakis-(pentafluorophenyl)borate,
N,N-dimethylbenzylammoniumtetrakis(pentafluorophenyl)borate,
N,N-dimethylaniliniumtetrakis(pentafluorophenyl)borate,
N,N-di(propyl)ammoniumtetrakis(pentafluorophenyl)borate,
di(cyclohexyl)ammoniumtetrakis(pentafluorophenyl)borate,
triphenylcarbeniumtetrakis(pentafluorophenyl)borate,
ferroceniumtetrakis(pentafluorophenyl)borate.

Preference is given to triphenylcarbeniumtetrakis(pentafluorophenyl) borate,
N,N-dimethylcyclohexylammoniumtetrakis(pentafluorophenyl)borate,
N,N-dimethylbenzylammoniumtetrakis(pentafluorophenyl) borate or
N,N-dimethylaniliniumtetrakis(pentafluorophenyl)borate.

It has been surprisingly found that certain boron cocatalysts are especially preferred. Preferred borates of use in the invention therefore comprise the trityl ion. Thus the use of N,N-dimethylammonium-tetrakispentafluorophenylborate and $Ph_3CB(PhF_5)_4$ and analogues therefore are especially favoured.

Suitable aluminium alkyl compounds are compounds of the formula (VIII) $AlR_3$ with R being a linear or branched $C_2$-$C_8$-alkyl group.

Preferred aluminium alkyl compounds are triethylaluminium, tri-isobutylaluminium, tri-isohexylaluminium, tri-n-octylaluminium and tri-isooctylaluminium.

According to the present invention it is possible to use only the aluminoxane cocatalyst optionally in the presence of an aluminium alkyl compound.

In a further embodiment it is possible to use the boron containing cocatalyst together with an aluminium alkyl compound in order to preactivate the boron containing cocatalyst by reaction thereof with the aluminium alkyl compound. This procedure is well known in the art.

Preferably an aluminoxane together with a boron based cocatalyst, optionally in the presence of an aluminium alkyl compound, are used in the catalyst system of the present invention.

Suitable amounts of cocatalyst will be well known to the skilled man.

The molar ratio of boron to the Hf ion of the metallocene may be in the range 0.5:1 to 10:1 mol/mol, preferably 1:1 to 10:1, especially 1:1 to 5:1 mol/mol.

The molar ratio of Al in the aluminoxane to the Hf ion of the metallocene may be in the range 1:1 to 2000:1 mol/mol, preferably 10:1 to 1000:1, more preferably 50:1 to 500:1 mol/mol.

Catalyst Manufacture

The metallocene complex of the present invention is used in combination with the cocatalyst(s) as a catalyst system for the polymerization of ethylene and $C_{4-10}$ alpha-olefin comonomer in a high temperature solution polymerization process.

The catalyst system of the invention can be used in non-supported form or in solid form. The catalyst system of the invention may be used as a homogeneous catalyst or heterogeneous catalyst.

The catalyst system of the invention in solid form, preferably in solid particulate form is free from an external carrier, however still being in solid form.

By free from an external carrier is meant that the catalyst does not contain an external support, such as an inorganic support, for example, silica or alumina, or an organic polymeric support material.

a) Non-Supported

Non-supported catalyst systems, suitable for the present invention can be prepared in solution, for example in an aromatic solvent like toluene, by contacting the metallocene (as a solid or as a solution) with the cocatalyst(s), for example methylaluminoxane and/or a borane or a borate salt previously dissolved in an aromatic solvent, or can be prepared by sequentially adding the catalyst components to the polymerization medium.

b) Solid Form

In an alternative embodiment, in order to provide the catalyst system of the invention in solid form but without using an external carrier, it is preferred if a liquid/liquid emulsion system is used. The process involves forming dispersing catalyst components (i) (the complex) and (ii)+ optionally (iii) (the cocatalysts) in a solvent, and solidifying said dispersed droplets to form solid particles.

In the present case, if, aluminoxane as well as boron based cocatalysts are used, it is particularly preferred if the aluminoxane is contacted with the metallocene before the borate is added. Both cocatalyst components and the metallocene are preferably present in one solution.

Full disclosure of the necessary process steps can be found in WO03/051934 which is herein incorporated by reference.

All or part of the preparation steps can be done in a continuous manner. Reference is made to WO2006/069733 describing principles of such a continuous or semicontinuous preparation methods of the solid catalyst types, prepared via emulsion/solidification method.

The formed catalyst preferably has good stability/kinetics in terms of longevity of reaction, high activity and the catalysts enable low ash contents.

The use of the heterogeneous, non-supported catalysts, (i.e. "self-supported" catalysts) might have, as a drawback, a tendency to dissolve to some extent in the polymerization media, i.e. some active catalyst components might leach out of the catalyst particles during slurry polymerization, whereby the original good morphology of the catalyst might be lost. These leached catalyst components are very active possibly causing problems during polymerization. Therefore, the amount of leached components should be minimized, i.e. all catalyst components should be kept in heterogeneous form.

Furthermore, the self-supported catalysts generate, due to the high amount of catalytically active species in the catalyst system, high temperatures at the beginning of the polymerization which may cause melting of the product material. Both effects, i.e. the partial dissolving of the catalyst system and the heat generation, might cause fouling, sheeting and deterioration of the polymer material morphology.

In order to minimise the possible problems associated with high activity or leaching, it is preferred to "prepolymerize" the catalyst before using it in polymerization process. It has to be noted that prepolymerization in this regard is part of the catalyst preparation process, being a step carried out after a solid catalyst is formed. This catalyst prepolymerization step is not part of the actual polymerization configuration, which might comprise a conventional process prepolymerization step as well. After the catalyst prepolymerization step, a solid catalyst is obtained and used in polymerization.

Catalyst "prepolymerization" takes place following the solidification step of the liquid-liquid emulsion process hereinbefore described. Prepolymerization may take place by known methods described in the art, such as that described in WO 2010/052263, WO 2010/052260 or WO 2010/052264. Preferable embodiments of this aspect of the invention are described herein.

Polymer

The polymer to be produced using the catalyst system of the invention is copolymer of ethylene and a $C_{4-10}$-alpha-olefin comonomer, like 1-butene, 1-hexene, 4-methyl-1-pentene, 1-octene etc. Preferably butene, hexene or octene and more preferably octene is used as comonomer.

The comonomer content in such a polymer may be up to 40 wt %, preferably between 5 to 40 wt %, more preferably 10 to 38 wt % and more preferable 15 to 36 wt %.

The density (measured according to ISO 1183-187) of the polymers is in the range of 0.850 g/cm$^3$ to 0.950 g/cm$^3$, preferably in the range of 0.850 g/cm$^3$ to 0.945 g/cm$^3$ and more preferably in the range of 0.850 g/cm$^3$ to 0.940 g/cm$^3$.

Mw/Mn value of the polymers of the invention is less than 5, e.g. in the range of 2.0 to 4.5.

The melting points (measured with DSC according to ISO 11357-3:1999) of the polymers to be produced are below 130° C., preferably below 120° C., more preferably below 110° C. and most preferably below 100° C.

Polymerization

The catalyst system of the present invention is used to produce the above defined ethylene copolymers in a high temperature solution polymerization process at temperatures higher than 100° C.

In view of this invention such process is essentially based on polymerizing the monomer and a suitable comonomer in a liquid hydrocarbon solvent in which the resulting polymer is soluble. The polymerization is carried out at a temperature above the melting point of the polymer, as a result of which a polymer solution is obtained. This solution is flashed in order to separate the polymer from the unreacted monomer and the solvent. The solvent is then recovered and recycled in the process.

A solution polymerization process is known for its short reactor residence times (compared to Gas-phase or slurry processes) allowing, thus, very fast grade transitions and significant flexibility in producing a wide product range in a short production cycle.

According to the present invention the used solution polymerization process is a high temperature solution polymerization process, using a polymerization temperature of higher than 100° C. Preferably the polymerization temperature is at least 110°, more preferably at least 150° C. The polymerization temperature can be up to 250° C.

The pressure in the used solution polymerization process according to the invention is preferably in a range of 10 to 100 bar, preferably 15 to 100 bar and more preferably 20 to 100 bar.

The liquid hydrocarbon solvent used is preferably a $C_{5-12}$-hydrocarbon which may be unsubstituted or substituted by $C_{1-4}$ alkyl group such as pentane, methyl pentane, hexane, heptane, octane, cyclohexane, methylcyclohexane and hydrogenated naphtha. More preferably unsubstituted $C_{6-10}$-hydrocarbon solvents are used.

A known solution technology suitable for the process according to the invention is the COMPACT technology.

Advantage

The new catalyst systems, comprising component (i), (ii) and (iii) can be advantageously used for ethylene copolymerization in high temperature solution polymerization process.

The catalyst systems according to the present invention show excellent comonomer incorporation and thermal stability compared to their Zr-analogues if used for ethylene copolymerization in high temperature solution polymerization process.

Applications

The polymers made by the catalyst system of the invention are useful in all kinds of end articles such as pipes, films (cast or blown films), fibers, moulded articles (e.g. injection moulded, blow moulded, rotomoulded articles), extrusion coatings and so on.

The invention will now be illustrated by reference to the following non-limiting examples

EXAMPLES

Methods
Al and Zr Determination (ICP-Method)

The elemental analysis of a catalyst was performed by taking a solid sample of mass, m. The catalyst was deactivated by substituting the inert storing conditions with ambient air, first passively through a needle and the actively by applying vacuum three times to the sampling container. Samples were dissolved to a volume V by first cooling on dry ice while adding freshly deionised water (5% of V) and nitric acid ($HNO_3$, 65%, 5% of V). The samples were transferred in full to volumetric flasks using deionised water and rinsing the sampling containers. Hydrofluoric acid (HF, 40%, 3% of V) was added to the volumetric flasks and volume V obtained by addition of freshly deionised water. The prepared sample solutions were left to stabilise for two hours.

The analysis was run at room temperature using a Thermo Elemental iCAP 6300 Inductively Coupled Plasma-Optical Emission Spectrometer (ICP-OES) which was calibrated using a blank (a solution of 5% HNO3, 5% HF in deionised water), and 6 standards of 0.5 ppm, 1 ppm, 10 ppm, 50 ppm, 100 ppm and 300 ppm of Al, with 0.5 ppm, 1 ppm, 5 ppm, 20 ppm, 50 ppm and 100 ppm of B and P in solutions of 5% HNO3, 3% HF in deionised water.

Immediately before analysis the calibration is 'resloped' using the blank and 100 ppm Al, 50 ppm B, P standard, a quality control sample (20 ppm Al, 5 ppm B, P in a solution of 5% HNO3, 3% HF in DI water) is run to confirm the reslope. The QC sample is also run after every 5th sample and at the end of a scheduled analysis set.

The reported values are an average of three successive aliquots taken from the same sample and are related back to the original catalyst by inputting the original mass of sample, m, and the dilution volume, V, into the software.

DSC Analysis

The melting point ($T_m$) and crystallization temperature ($T_c$) were determined on a DSC200 TA instrument, by placing a 5-7 mg polymer sample, into a closed DSC aluminum pan, heating the sample from −30° C. to 180° C. at 10° C./min, holding for 5 min at 180° C., cooling from 180° C. to −30° C., holding for 5 min at −30° C., heating from −30° C. to 180° C. at 10° C./min. The reported $T_m$ is the maximum of the curve from the second heating scan and $T_c$ is the maximum of the curve of the cooling scan.

Quantification of Comonomer Content by NMR Spectroscopy

Quantitative nuclear-magnetic resonance (NMR) spectroscopy was used to quantify the comonomer content of the polymers.

Quantitative $^{13}C\{^1H\}$ NMR spectra recorded in the molten-state using a Bruker Advance III 500 NMR spectrometer operating at 500.13 and 125.76 MHz for $^1H$ and $^{13}C$ respectively. All spectra were recorded using a $^{13}C$ optimised 7 mm magic-angle spinning (MAS) probehead at 150° C. using nitrogen gas for all pneumatics. Approximately 200 mg of material was packed into a 7 mm outer diameter zirconia MAS rotor and spun at 4 kHz. This setup was chosen primarily for the high sensitivity needed for rapid identification and accurate quantification. {klimke06, parkinson07, castignolles09, parkinson11} Standard single-pulse excitation was employed utilising the transient NOE at short recycle delays of 3 s {pollard04, klimke06} and the RS-HEPT decoupling scheme{fillip05,griffin07}. A total of 1024 (1 k) transients were acquired per spectrum. This setup was chosen due its high sensitivity towards low comonomer contents.

Quantitative $^{13}C\{^1H\}$ NMR spectra were processed, integrated and quantitative properties determined using custom spectral analysis automation programs. All chemical shifts are internally referenced to the bulk methylene signal (δ+) at 30.00 ppm {randall89}.

Characteristic signals corresponding to the incorporation of 1-octene were observed (randall89, liu01, qiu07) and all comonomer contents calculated with respect to all other monomers present in the polymer.

Characteristic signals resulting from isolated 1-octene incorporation i.e. EEOEE comonomer sequences, were observed. Isolated 1-octene incorporation was quantified using the integral of the signal at 38.32 ppm. This integral is assigned to the unresolved signals corresponding to both $*B6$ and $*\beta B6B6$ sites of isolated (EEOEE) and isolated double non-consecutive (EEOEOEE) 1-octene sequences respectively. To compensate for the influence of the two $*\beta B6B6$ sites the integral of the $\beta\beta B6B6$ site at 24.7 ppm is used:

$$O = I_{*B6+*\beta B6B6} - 2*I_{\beta\beta B6B6}$$

Characteristic signals resulting from consecutive 1-octene incorporation, i.e. EEOOEE comonomer sequences, were also observed. Such consecutive 1-octene incorporation was quantified using the integral of the signal at 40.48 ppm assigned to the ααB6B6 sites accounting for the number of reporting sites per comonomer:

$$OO=2*I_{\alpha\alpha B6B6}$$

Characteristic signals resulting from isolated non-consecutive 1-octene incorporation, i.e. EEOEOEE comonomer sequences, were also observed. Such isolated non-consecutive 1-octene incorporation was quantified using the integral of the signal at 24.7 ppm assigned to the ββB6B6 sites accounting for the number of reporting sites per comonomer:

$$OEO=2*I_{\beta\beta B6B6}$$

Characteristic signals resulting from isolated triple-consecutive 1-octene incorporation, i.e. EEOOOEE comonomer sequences, were also observed. Such isolated triple-consecutive 1-octene incorporation was quantified using the integral of the signal at 41.2 ppm assigned to the ααγB6B6B6 sites accounting for the number of reporting sites per comonomer:

$$OOO=3/2*I_{\alpha\alpha\gamma B6B6B6}$$

With no other signals indicative of other comonomer sequences observed the total 1-octene comonomer content was calculated based solely on the amount of isolated (EEOEE), isolated double-consecutive (EEOOEE), isolated non-consecutive (EEOEOEE) and isolated triple-consecutive (EEOOOEE) 1-octene comonomer sequences:

$$O_{total}=O+OO+OEO+OOO$$

Characteristic signals resulting from saturated end-groups were observed. Such saturated end-groups were quantified using the average integral of the two resolved signals at 22.84 and 32.23 ppm. The 22.84 ppm integral is assigned to the unresolved signals corresponding to both 2B6 and 2S sites of 1-octene and the saturated chain end respectively. The 32.23 ppm integral is assigned to the unresolved signals corresponding to both 3B6 and 3S sites of 1-octene and the saturated chain end respectively. To compensate for the influence of the 2B6 and 3B6 1-octene sites the total 1-octene content is used:

$$S=(1/2)*(I_{2S+2B6}+I_{3S+3B6}-2*O_{total})$$

The ethylene comonomer content was quantified using the integral of the bulk methylene (bulk) signals at 30.00 ppm. This integral included the γ and 4B6 sites from 1-octene as well as the δ$^+$ sites. The total ethylene comonomer content was calculated based on the bulk integral and compensating for the observed 1-octene sequences and end-groups:

$$E_{total}=(1/2)*[I_{bulk}+2*O+1*OO+3*OEO+0*OOO+3*S]$$

It should be noted that compensation of the bulk integral for the presence of isolated triple-incorporation (EEOOOEE) 1-octene sequences is not required as the number of under and over accounted ethylene units is equal.

The total mole fraction of 1-octene in the polymer was then calculated as:

$$fO=(O_{total}/(E_{total}O_{total}))$$

The total comonomer incorporation of 1-octene in weight percent was calculated from the mole fraction in the standard manner:

$$O\ [wt\ \%]=100*(fO*112.21)/((fO*112.21)+((1-fO)*28.05))$$

klimke06
Klimke, K., Parkinson, M., Piel, C., Kaminsky, W., Spiess, H. W., Wilhelm, M., Macromol. Chem. Phys. 2006; 207:382.
parkinson07
Parkinson, M., Klimke, K., Spiess, H. W., Wilhelm, M., Macromol. Chem. Phys. 2007; 208:2128.
parkinson11
NMR Spectroscopy of Polymers: Innovative Strategies for Complex Macromolecules, Chapter 24, 401 (2011)
pollard04
Pollard, M., Klimke, K., Graf, R., Spiess, H. W., Wilhelm, M., Sperber, O., Piel, C., Kaminsky, W., Macromolecules 2004; 37:813.
filip05
Filip, X., Tripon, C., Filip, C., J. Mag. Resn. 2005, 176, 239
griffin07
Griffin, J. M., Tripon, C., Samoson, A., Filip, C., and Brown, S. P., Mag. Res. in Chem. 2007 45, 51, S198
castignolles09
Castignolles, P., Graf, R., Parkinson, M., Wilhelm, M., Gaborieau, M., Polymer 50 (2009) 2373
zhou07
Zhou, Z., Kuemmerle, R., Qiu, X., Redwine, D., Cong, R., Taha, A., Baugh, D. Winniford, B., J. Mag. Reson. 187 (2007) 225
busico07
Busico, V., Carbonniere, P., Cipullo, R., Pellecchia, R., Severn, J., Talarico, G., Macromol. Rapid Commun. 2007, 28, 1128
randall89
J. Randall, Macromol. Sci., Rev. Macromol. Chem. Phys. 1989, C29, 201.
qui07
Qiu, X., Redwine, D., Gobbi, G., Nuamthanom, A., Rineldi, P., Macromolecules 2007, 40, 6879
liu01
Liu, W., Rineldi, P., McIntosh, L., Quirk, P., Macromolecules 2001, 34, 4757
GPC: Molecular Weight Averages, Molecular Weight Distribution, and Polydispersity Index ($M_n$, $M_w$, $M_w/M_n$)

Molecular weight averages (Mw, Mn), Molecular weight distribution (MWD) and its broadness, described by polydispersity index, PDI=Mw/Mn (wherein Mn is the number average molecular weight and Mw is the weight average molecular weight) were determined by Gel Permeation Chromatography (GPC) according to ISO 16014-4:2003 and ASTM D 6474-99. A Waters GPCV2000 instrument, equipped with differential refractive index detector and online viscosimeter was used with 2×GMHXL-HT and 1× G7000HXL-HT TSK-gel columns from Tosoh Bioscience and 1,2,4-trichlorobenzene (TCB, stabilized with 250 mg/L 2,6-Di tert butyl-4-methyl-phenol) as solvent at 140° C. and at a constant flow rate of 1 mL/min. 209.5 μL of sample solution were injected per analysis. The column set was calibrated using universal calibration (according to ISO 16014-2:2003) with at least 15 narrow MWD polystyrene (PS) standards in the range of 1 kg/mol to 12000 kg/mol. Mark Houwink constants for PS, PE and PP used are as per ASTM D 6474-99. All samples were prepared by dissolving 0.5-4.0 mg of polymer in 4 mL (at 140° C.) of stabilized TCB (same as mobile phase) and keeping for max. 3 hours at max. 160° C. with continuous gentle shaking prior sampling into the GPC instrument.

Chemicals

MAO was purchased from Chemtura and used as a 30 wt-% solution in toluene.

Triphenylcarbeniumtetrakis(pentafluorophenyl)borate (alternative name trityl tetrakis-(pentafluorophenyl)borate) (CAS 136040-19-2) was purchased from Acros (tritylBF20)

1-octene as co-monomer (99%, Sigma Aldrich) was dried over molecular sieves and degassed with nitrogen before use.

Heptane and decane (99.9%, Sigma Aldrich) were dried under molecular sieves and degassed with nitrogen before use.

Catalyst Preparation Examples

For the purpose of this invention, the terms dimethylsilyl, dimethylsilanediyl and dimethylsililene are equivalent.
a) Complex Preparation:
1. Complex 1-Hf: anti-dimethylsilylene(2-methyl-4-phenyl-5-methoxy-6-tert-butyl-indenyl)(2-methyl-4-(4-tert-butyl-phenyl)indenyl)hafnium dichloride (C1-Hf) was prepared in the same way as described in the patent application WO2013/007650A1 by using $HfCl_4$ instead of $ZrCl_4$. Thus, the yield of the anti-hafnocene isolated in this synthesis was 15%.
2. As Comparative Example Complex 1-Zr was used: anti-dimethylsilylene(2-methyl-4-phenyl-5-methoxy-6-tert-butyl-indenyl)(2-methyl-4-(4-tert-butyl-phenyl)indenyl)zirconium dichloride (C1-Zr) was prepared as described in the patent application WO2013/007650A1
3. Complex 2-Hf: anti-dimethylsilylene(2-methyl-4-(3,5-di-tert-butylphenyl)-7-methyl-indenyl)(2-methyl-4-(4-tert-butyl-phenyl)indenyl)hafnium dichloride (C2-Hf) was prepared according to the following procedure:

3.a) 5-Bromo-2-methylbenzaldehyde

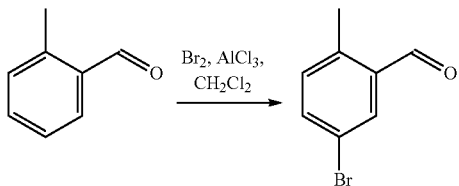

To a suspension of 344 g (2.58 mol, 1.5 eq.) of $AlCl_3$ in 1100 cm³ of dichloromethane 206.8 g (1.72 mol) of 2-methylbenzaldehyde was added dropwise by vigorous stirring for 15 min at 5° C. The resulting mixture was stirred for 15 min at 5° C., and then 88.9 ml (276 g, 1.73 mol) of bromine was added for 1 h at this temperature. The final mixture was additionally stirred for 6 h at room temperature and then poured on 2 kg of ice. The organic layer was separated, the aqueous layer was extracted with 2×200 ml of dichloromethane. The combined organic extract was washed by aqueous $NaHCO_3$, dried over $Na_2SO_4$, and then evaporated to dryness to yield reddish liquid. This crude product was distilled in vacuum, b.p. 100-120° C./5 mm Hg. The obtained colorless liquid (which crystallizes at 5° C.) was dissolved in 900 ml of n-hexane. Crystals precipitated from this solution for 3 days at 5° C. were collected and dried in vacuum. On the evidence of NMR spectroscopy this mixture consists of 5-bromo-2-methylbenzaldehyde and 3-bromo-2-methylbenzaldehyde in ratio equal ca. 3 to 1. This mixture was recrystallized from 500 ml of hot n-hexane. White crystals precipitated at 5° C. were collected, washed by 150 ml of cold (+5° C.) n-hexane, and dried in vacuum (~60° C./20 mm Hg) to give colorless liquid which crystallizes at room temperature. Yield 80.9 g (24%) of 5-bromo-2-methylbenzaldehyde including ca. 2% of 3-bromo-2-methylbenzaldehyde.

Anal. calc. for $C_8H_7BrO$: C, 48.27; H, 3.54. Found: C, 48.05; H, 3.41.

$^1H$ NMR ($CDCl_3$): δ 10.21 (s, 1H, CHO), 7.90 (d, J=2.2 Hz, 1H, 6-H), 7.57 (dd, J=8.2 Hz, J=2.3 Hz, 1H, 4-H), 7.14 (d, J=8.2 Hz, 1H, 3-H), 2.61 (s, 3H, Me). $^{13}C\{^1H\}$ NMR ($CDCl_3$): δ 191.0, 139.3, 136.4, 135.5, 134.1, 133.4, 120.0, 18.85.

3.b) 5-Bromo-2-methylbenzyl chloride

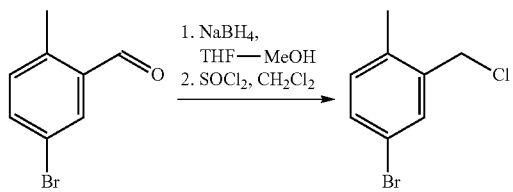

To a mixture of 80.9 g (0.406 mol) of 5-bromo-2-methylbenzaldehyde and 7.80 g (0.206 mol) of $NaBH_4$ in 300 ml of THF 200 ml of methanol was added dropwise by vigorous stirring for 5 h at 0-5° C. This mixture was stirred overnight at room temperature and then added to 1 liter of cold water. The resulting mixture was acidified by 2 M HCl to pH-1, and the formed (5-bromo-2-methylphenyl)methanol was extracted with 3×250 ml of dichloromethane. The combined organic extract was dried over $Na_2SO_4$ and evaporated to dryness. To the residue dissolved in 450 ml of dichloromethane 37 ml of $SOCl_2$ was added dropwise at +5° C. The resulting solution was stirred overnight at room temperature, evaporated to dryness, the residue was dissolved in 500 ml $CH_2Cl_2$, and the obtained solution was washed with 500 ml of water. The organic layer was separated, the aqueous layer was additionally extracted with 2×100 ml of dichloromethane. The combined organic extract was passed through a short pad of silica gel 60 (40-63 um), the filtrate was evaporated to dryness, and the residue was dried in vacuum to yield 5-bromo-2-methylbenzyl chloride as a slightly yellowish liquid which was further used without an additional purification.

Anal. calc. for $C_8H_8BrCl$: C, 43.77; H, 3.67. Found: C, 43.89; H, 3.80.

$^1H$ NMR ($CDCl_3$): δ 7.45 (d, J=2.0 Hz, 1H, 3-H), 7.35 (dd, J=8.2 Hz, J=2.0 Hz, 1H, 5-H), 7.06 (d, J=8.2 Hz, 1H, 6-H), 4.53 (s, 2H, $CH_2Cl$), 2.36 (s, 3H, Me). $^{13}C\{^1H\}$ NMR ($CDCl_3$): δ 137.5, 136.0, 132.4, 132.3, 131.7, 119.5, 43.8, 18.3.

3.c) 3-(5-Bromo-2-methylphenyl)-2-methylpropanoyl chloride

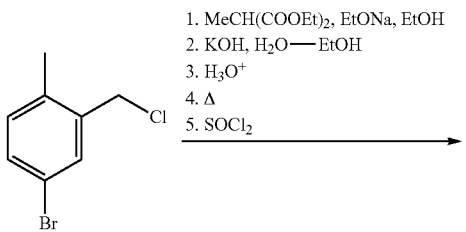

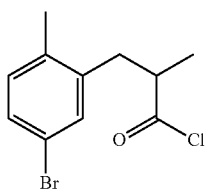

In a three-necked round-bottom flask 9.50 g (0.413 mol) of sodium metal was dissolved in 260 ml of dry ethanol. To the resulting solution 72.0 g (0.413 mol) of diethyl methylmalonate was added. This mixture was stirred for 15 min, then 5-bromo-2-methylbenzyl chloride prepared above was added by vigorous stirring at such a rate as to maintain gentle reflux. This mixture was refluxed for an additional 2 h and then cooled to room temperature. A solution of 85 g of KOH in 250 ml of water was added. The resulting mixture was refluxed for 4 h to saponificate the ester formed. Ethanol and water were distilled off until temperature reached 95° C., and 1000 ml of water and then 12 M HCl (to pH 1) were added to the residue. The precipitated substituted methylmalonic acid was filtered off, washed with 3×100 ml of water, and then decarboxylated at 180° C. to give 3-(5-bromo-2-methylphenyl)-2-methylpropanoic. A mixture of this acid and 105 ml of SOCl$_2$ was stirred at room temperature for 24 hours. After evaporation of an excess of thionyl chloride, the residue was distilled in vacuum to give 85.3 g (75% from 5-bromo-2-methylbenzaldehyde) 3-(5-bromo-2-methylphenyl)-2-methylpropanoyl chloride, b.p. 115° C./1 mm Hg.

Anal. calc. for $C_{11}H_{12}BrClO$: C, 47.94; H, 4.39. Found: C, 48.12; H, 4.45.

$^1$H NMR (CDCl$_3$): δ7.28-7.26 (m, 2H, 6,4-H in Ph), 7.03 (d, J=7.7 Hz, 1H, 3-H in Ph), 3.18 (dd, J=13.8 Hz, J=5.9 Hz, 1H, ArCHH'), 3.10 (m, 1H, CHCOCl), 2.65 (dd, J=13.8 Hz, J=8.1 Hz, 1H, ArCHH), 2.28 (s, 3H, ArMe), 1.29 (d, J=6.7 Hz, 3H, CHMe). $^{13}$C{$^1$H} NMR (CDCl$_3$): δ 176.9, 138.1, 135.2, 132.4, 132.2, 130.0, 119.5, 51.8, 36.1, 19.0, 16.6.

3.d) 2,4-dimethyl-7-Bromo-indan-1-one

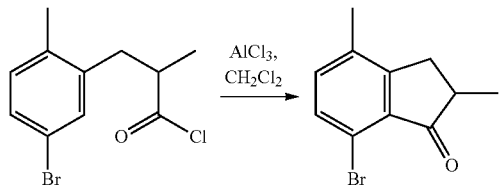

To a stirred suspension of 49.5 g (0.371 mol, 1.2 eq.) of AlCl$_3$ in 300 ml of dichloromethane a solution of 85.3 g (0.310 mol) of 3-(5-bromo-2-methylphenyl)-2-methylpropanoyl chloride in 50 ml of dichloromethane was added dropwise. This mixture was stirred overnight at room temperature and then poured on 500 g of ice. The organic layer was separated, and the aqueous layer was additionally extracted with 3×75 ml of dichloromethane. The combined organic extract was washed by aqueous K$_2$CO$_3$, dried over K$_2$CO$_3$, passed through a short pad of silica gel, and then evaporated to dryness. This procedure gave 74.0 g (>99%) of 2,4-dimethyl-7-bromo-indan-1-one as a light-orange liquid, solidified at room temperature, which was further used without an additional purification.

Anal. calc. for $C_{11}H_{11}BrO$: C, 55.25; H, 4.64. Found: C, 55.40; H, 4.81.

$^1$H NMR (CDCl$_3$): δ 7.41 (d, J=8.0 Hz, 1H, 6-H in indan-1-one), 7.21 (d, J=8.0 Hz, 1H, 5-H in indan-1-one), 3.24 (dd, J=17.3 Hz, J=7.9 Hz, 3-H in indan-1-one), 2.73 (m, 1H, 2-H in indan-1-one), 2.54 (dd, J=17.3 Hz, J=4.1 Hz, 1H, 3'-H in indan-1-one), 2.29 (s, 3H, 4-Me in indan-1-one), 1.33 (d, J=7.3 Hz, 3H, 2-Me in indan-1-one). $^{13}$C{$^1$H} NMR (CDCl$_3$): δ 207.0, 155.0, 135.6, 134.8, 133.1, 132.3, 116.5, 42.4, 33.0, 17.4, 16.4.

3.e) 1-methoxy-2,4-dimethyl-7-Bromoindane

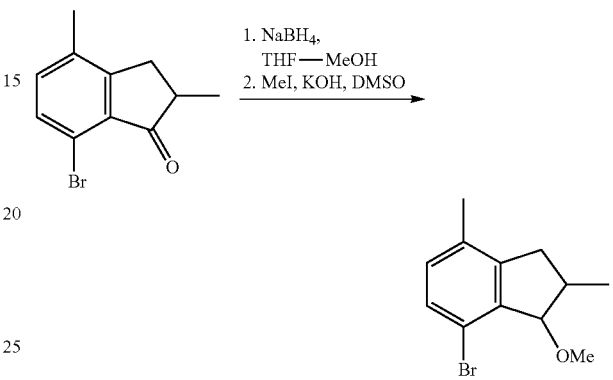

To a mixture of 74.0 g (0.310 mol) of 2,4-dimethyl-7-bromoindan-1-one and 5.86 g (0.155 mol) of NaBH$_4$ in 310 ml of THF 155 ml of methanol was added dropwise by vigorous stirring for 5 h at 0-5° C. This mixture was stirred overnight at room temperature and then added to 1 liter of cold water. The resulting mixture was acidified by 2 M HCl to pH-5, and then it was extracted with 3×250 ml of dichloromethane. The combined organic extract was dried over Na$_2$SO$_4$ and evaporated. The resulting orange oil was dissolved in 600 ml of DMSO, then 70 g (1.25 mol) of KOH and 88 g (0.62 mol) of MeI were added to the resulting solution. This mixture was stirred for 3 h at ambient temperature. Further on, the solution was decanted from an excess of KOH, the latter was washed with 2×200 ml of dichloromethane, and 2000 cm$^3$ of water was added to the combined solution. The organic layer was separated, and the aqueous layer was additionally extracted with 2×100 ml of dichloromethane. The combined organic extract was additionally washed with 5×1500 ml of water, dried over Na$_2$SO$_4$, and evaporated to dryness. Fractional distillation of the residue in vacuum gave 72.3 g (92%) of 1-methoxy-2,4-dimethyl-7-bromoindane, b.p. 107-112° C./5 mm Hg.

Anal. calc. for $C_{12}H_{15}BrO$: C, 56.49; H, 5.93. Found: C, 56.43; H, 6.02.

$^1$H NMR (CDCl$_3$): δ7.26 (d, J=8.6 Hz, 1H, 6-H of anti-isomer), 7.24 (d, J=8.6 Hz, 1H, 6-H of syn-isomer), 6.94 (d, J=8.6 Hz, 1H, 5H of anti-isomer), 6.92 (d, J=8.6 Hz, 1H, 5H of syn-isomer), 4.57 (d, J=5.5 Hz, 1H, 1-H of syn-isomer), 4.42 (m, 1H, 1-H of anti-isomer), 3.53 (s, 3H, OMe of syn-isomer), 3.45 (s, 3H, OMe of anti-isomer), 3.27 (dd, J=16.6 Hz, J=7.3 Hz, 1H, 3-H of anti-isomer), 2.87 (dd, J=15.7 Hz, J=7.5 Hz, 1H, 3-H of syn-isomer), 2.68 (dd, J=15.7 Hz, J=9.8 Hz, 1H, 3'-H of syn-isomer), 2.57 (m, 1H, 2-H of anti-isomer), 2.44 (m, 1H, 2-H of syn-isomer), 2.39 (dd, J=16.6 Hz, J=1.4 Hz, 3'-H of anti-isomer), 2.18 (s, 6H, 4-Me of syn- and anti-isomers), 1.26 (d, J=6.9 Hz, 3H, 2-Me of syn-isomer), 1.05 (d, J=7.3 Hz, 2-Me of anti-isomer).

3.f) 2,7-dimethyl-4-(3,5-Di-tert-butylphenyl)-1H-indene

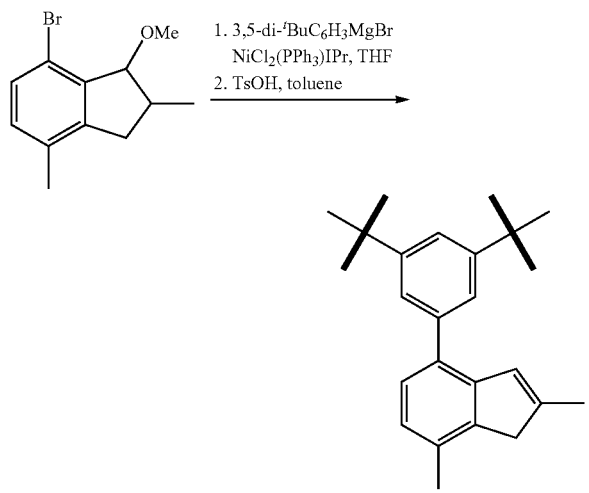

To a solution of 3,5-di-tert-butylphenylmagnesium bromide obtained from 59.0 g (0.219 mol) of 1-bromo-3,5-di-tert-butylbenzene and 9.31 g (0.383 mol, 1.75 eq.) of magnesium turnings in 550 ml of THF 1.0 g (1.28 mmol, 0.71 mol. %) NiCl$_2$(PPh$_3$)IPr and a solution of 46.1 g (0.181 mol) of 1-methoxy-2,4-dimethyl-7-bromoindane in 50 ml of THF were added. A moderate reflux occurs approximately after one minute which ceased after the following 30 sec. This mixture was refluxed additionally for 1 h. Finally, 50 ml of water was added, and the main part of THF was distilled off on rotary evaporator. Further on, 500 ml of dichloromethane and 500 ml of 2 M HCl were added to the residue. The organic layer was separated, the aqueous layer was additionally extracted with 100 ml of dichloromethane. The combined organic extract was evaporated to dryness to give a yellowish oil. To a solution of this oil in 700 ml of toluene 0.8 g of TsOH was added. The resulting mixture was refluxed using Dean-Stark head for 20 min, one more portion (0.8 g) of TsOH was added, and the mixture was refluxed for another 20 min. The resulting mixture cooled to room temperature was washed with 200 ml of 10% aqueous NaHCO$_3$. The organic layer was separated, the aqueous layer was additionally extracted with 2×100 ml of dichloromethane. The combined organic extract was evaporated to dryness, a solution of the residue in 500 ml of dichloromethane was passed through a short pad of silica gel 60 (40-63 um) and then evaporated to dryness to give yellowish crystalline material. This crude product was re-crystallization from 200 ml of hot n-hexane. Crystals precipitated from this solution at 5° C. were collected and dried in vacuum. This procedure gave 49.8 g of white microcrystalline product. The mother liquor was evaporated to dryness, and the main part of 1,3-di-tert-butylbenzene was distilled off at elevated temperature on rotary evaporator. The residue was then re-crystallized from 80 ml of hot n-hexane. This gave additional 6.21 g of the product. Thus, the total yield of 2,7-dimethyl-4-(3,5-di-tert-butylphenyl)-1H-indene was 56.0 g (93%).

Anal. calc. for C$_{25}$H$_{32}$: C, 90.30; H, 9.70. Found: C, 90.44; H, 9.89.

$^1$H NMR (CDCl$_3$): δ (t, J=1.8 Hz, 1H, 4-H in C$_6$H$_3$$^t$Bu$_2$), 7.33 (d, J=1.8 Hz, 2H, 2,6-H in C$_6$H$_3$$^t$Bu$_2$), 7.24 (d, J=7.7 Hz, 1H, 5-H in indenyl), 7.01 (d, J=7.7 Hz, 1H, 6-H in indenyl), 6.67 (m, 1H, 3-H in indenyl), 3.27 (s, 2H, 1-H in indenyl), 2.37 (s, 3H, 7-Me in indenyl), 2.16 (s, 3H, 2-Me in indenyl), 1.37 (s, 18H, $^t$Bu). $^{13}$C{$^1$H} NMR (CDCl$_3$): δ 150.5, 146.0, 143.1, 142.4, 140.2, 133.0, 131.3, 127.2, 126.7, 125.2, 123.3, 120.4, 42.0, 34.9, 31.5, 18.5, 17.0.

3.g) [2-methyl-4-(4-tert-Butylphenyl)-1H-inden-1-yl](chloro)dimethylsilane

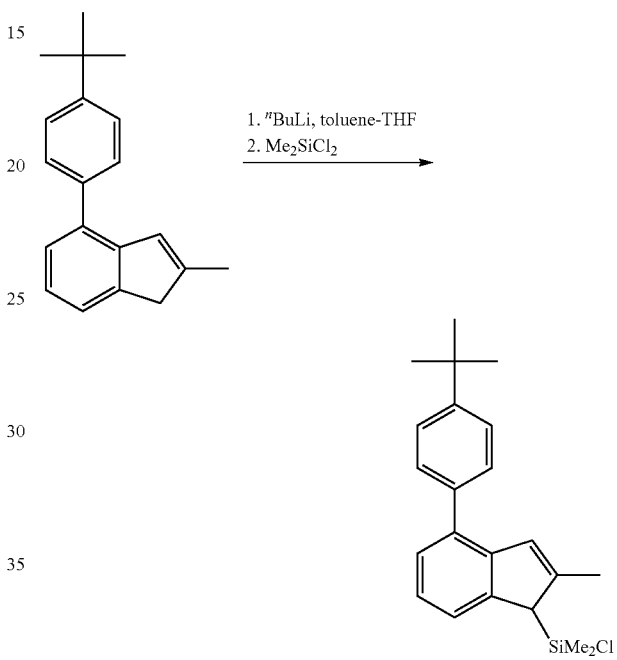

To a solution of 9.84 g (37.5 mmol) of 2-methyl-7-(4-tert-butylphenyl)-1H-indene in a mixture of 200 ml of toluene and 10 ml of THF 15.0 ml (37.5 mmol) of 2.5 M $^n$BuLi in hexanes was added at room temperature. The resulting solution was stirred for 2 h at 60° C., then cooled to 0° C., and 24.0 g (186 mmol, 5 eq.) of dichlorodimethylsilane was added in one portion. The formed solution was refluxed for 1 h, then evaporated to ca. 150 ml, and filtered through glass frit (G3). The precipitate was additionally washed by 2×30 ml of toluene. The combined filtrate was evaporated to dryness to give [2-methyl-4-(4-tert-butylphenyl)-1H-inden-1-yl](chloro)dimethylsilane as viscous yellowish oil which was further used without an additional purification.

Anal. calc. for C$_{22}$H$_{27}$ClSi: C, 74.44; H, 7.67. Found: C, 74.75; H, 7.89.

$^1$H NMR (CDCl$_3$): δ7.54 (m, 4H, 2,3,5,6-H in C$_6$H$_4$$^t$Bu), 7.49 (d, J=7.5 Hz, 1H, 7-H in indenyl), 7.35 (d, J=7.3 Hz, 5-H in indenyl), 7.24 (t, J=7.5, 6-H in indenyl), 6.91 (m, 1H, 3-H in indenyl), 3.72 (s, 1H, 1-H in indenyl), 2.33 (s, 3H, 2-Me in indenyl), 1.45 (s, 9H, $^t$Bu), 0.49 (s, 3H, SiMeMe'), 0.24 (s, 3H, SiMeMe'). $^{13}$C{$^1$H} NMR (CDCl$_3$): δ 149.7, 146.1, 143.1, 142.9, 138.1, 134.1, 128.5, 126.7, 126.1, 125.3, 123.3, 122.3, 50.4, 34.5, 31.4, 17.6, 1.0, 0.7.

3.h) A mixture of [2-methyl-4-(4-tert-butylphenyl)-1H-inden-1-yl][2,7-dimethyl-4-(3,5-di-tert-butylphenyl)-1H-inden-1-yl]dimethylsilane and [2-methyl-4-(4-tert-butylphenyl)-1H-inden-1-yl] [2,4-di methyl-7-(3,5-di-tert-butylphenyl)-1H-inden-1-yl]dimethylsilane

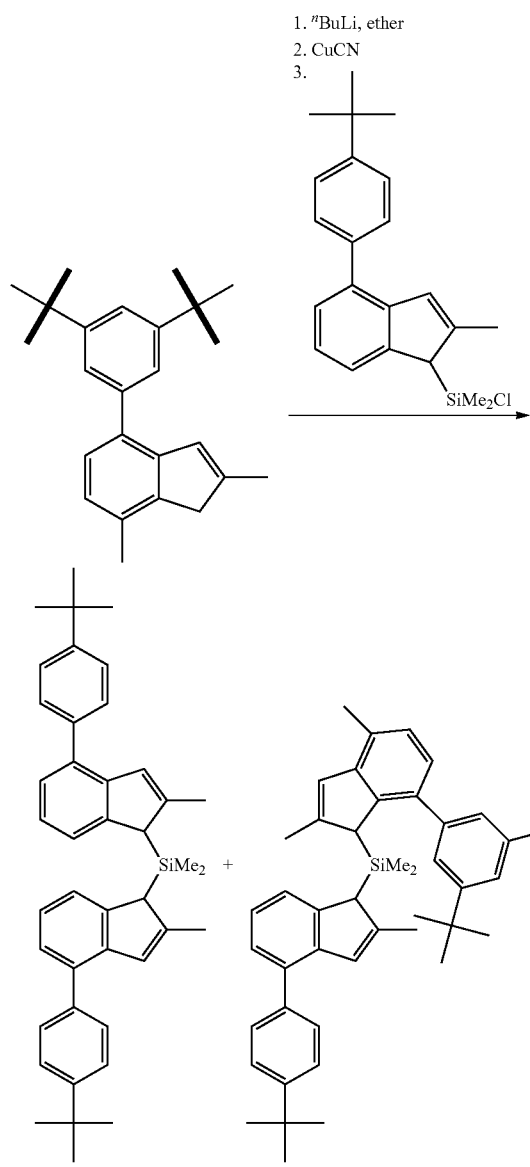

To a solution of 12.5 g (37.5 mmol) of 2,7-dimethyl-4-(3,5-di-tert-butylphenyl)-1H-indene in 200 ml of ether 15.0 ml (37.5 mmol) of 2.5 M ⁿBuLi in hexanes was added in one portion at −40° C. The resulting mixture was stirred overnight at room temperature, then cooled to −40° C., and 1.68 g (18.8 mmol, 0.5 eq.) of CuCN was added. The formed mixture was stirred for 1 h at −20° C., then cooled to −40° C., and then a solution 13.3 g (37.5 mmol) of [2-methyl-4-(4-tert-butylphenyl)-1H-inden-1-yl](chloro)dimethylsilane in 200 ml of ether was added in one portion. Further on, this mixture was stirred overnight at ambient temperature, and then 0.5 ml of water was added. The formed mixture was filtered through a pad of silica gel 60 (40-63 um) which was additionally washed by dichloromethane. The combined organic elute was evaporated to dryness and dried in vacuum. This procedure gave 24.0 g (36.9 mmol, 98%) of a mixture of [2-methyl-4-(4-tert-butylphenyl)-1H-inden-1-yl][2,7-dimethyl-4-(3,5-di-tert-butylphenyl)-1H-inden-1-yl]dimethylsilane and [2-methyl-4-(4-tert-butylphenyl)-1H-inden-1-yl][2,4-dimethyl-7-(3,5-di-tert-butylphenyl)-1H-inden-1-yl]dimethylsilane (>90% purity by NMR spectroscopy; ca. 1:1 mixture of the regioisomers) as yellowish glass which was further used without an additional purification.

Anal. calc. for $C_{47}H_{58}Si$: C, 86.71; H, 8.98. Found: C, 86.92; H, 9.12.

$^1$H NMR (CDCl$_3$): δ 7.52-7.36 (m), 7.31-6.93 (m), 6.83 (s), 6.80 (s), 6.77 (s), 6.74 (s), 6.73 (s), 6.61 (s), 6.59 (s), 4.41 (s), 4.32 (s), 4.00 (s), 3.90 (s), 3.74 (s), 3.73 (s), 3.11 (s), 2.94 (s), 2.46 (s), 2.45 (s), 2.39 (s), 2.30 (s), 2.29 (s), 2.28 (s), 2.24 (s), 2.22 (s), 2.10 (s), 1.91 (s), 1.81 (s), 1.39 (s), 1.38 (s), 1.37 (s), 1.35 (s), 1.33 (s), 1.29 (s), −0.17 (s), −0.26 (s), −0.26 (s), −0.59 (s), −0.62 (s), −0.68 (s), −0.69 (s).

3.i) Dimethylsilanediyl[2-methyl-4-(4-tert-butylphenyl)inden-1-yl][2,7-dimethyl-4-(3,5-di-tert-butylphenyl)inden-1-yl]hafnium dichloride

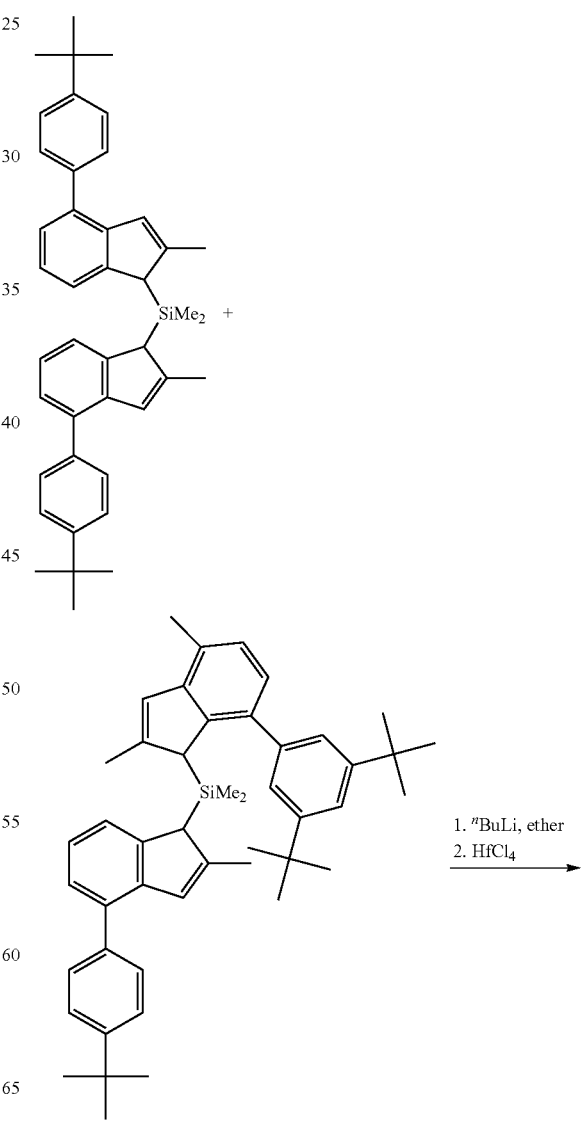

-continued

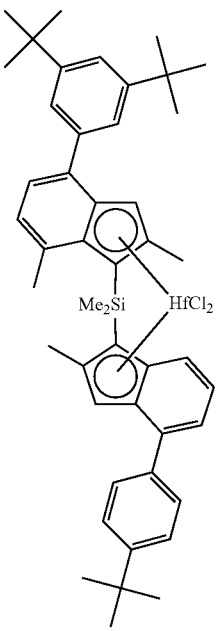

To a solution of 24.0 g (36.9 mmol, >90% purity) of a mixture of [2-methyl-4-(4-tert-butylphenyl)-1H-inden-1-yl][2,7-dimethyl-4-(3,5-di-tert-butylphenyl)-1H-inden-1-yl]dimethylsilane and [2-methyl-4-(4-tert-butylphenyl)-1H-inden-1-yl][2,4-dimethyl-7-(3,5-di-tert-butylphenyl)-1H-inden-1-yl]dimethylsilane (as described above) in 250 ml of ether 29.5 ml (73.8 mmol) of 2.5 M nBuLi in hexanes was added in one portion at −20° C. This mixture was stirred overnight at room temperature, then cooled to −60° C., and 11.8 g (36.9 mmol) of HfCl$_4$ was added. The resulting mixture was stirred for 24 h, then filtered through glass frit (G4), and the precipitate was washed with 30 ml of ether. On the evidence of NMR spectroscopy, this precipitate was pure syn-zirconocene while the filtrate included a mixture of three isomeric complexes, i.e. the desired anti-hafnocene (55%), anti-hafnocene (25%), and one more isomeric ansa-hafnocene of unknown structure (20%). The precipitate was dissolved in 100 ml of hot toluene, and the formed suspension was filtered through glass frit (G4). The filtrate was evaporated to ca. 30 ml and then heated to obtain clear solution. Crystals precipitated from this solution at room temperature were collected, washed by 15 ml of cold n-hexane, and then dried in vacuum. This procedure gave 4.30 g (13%) of pure syn-complex. The mother liquor was evaporated to ca. 5 ml, and 80 ml of n-hexane was added. Crystals precipitated from the formed solution at room temperature were collected and dried in vacuum. This procedure gave 1.38 g (4%) of syn-complex contaminated with ca. 8% of anti-isomer. The mother liquor was evaporated to dryness, the residue was re-crystallized from 40 ml of hot n-hexane. Crystals precipitated from this solution after 4 h at room temperature were collected and dried in vacuum to give 0.28 g (1%) of the desired anti-complex contaminated with ca. 5% of syn-isomer. Additional crystalline material was obtained from the mother liquor after 3 days at room temperature. These crystals were collected and dried in vacuum to give 1.31 g (4%) of anti-complex of ca. 93% purity (i.e. 7% of unknown impurity). Assignment in NMR spectra was made using the following abbreviations: L$^1$ for 2-methyl-4-(4-tert-butylphenyl)-1H-inden-1-yl and L$^2$ for 2,7-dimethyl-4-(3,5-di-tert-butylphenyl)-1H-inden-1-yl. anti-Hafnocene.

Anal. calc. for C$_{47}$H$_{56}$Cl$_2$HfSi: C, 62.83; H, 6.28. Found: C, 62.87; H, 6.39.
$^1$H NMR (CDCl$_3$): δ7.69 (d, J=8.5 Hz, 1H, 7-H in L$^1$), 7.58-7.56 (m, 2H, 2,6-H in C$_6$H$_4$$^t$Bu), 7.48 (d, J=1.1 Hz, 2H, 2,6-H in C$_6$H$_3$$^t$Bu$_2$), 7.46-7.44 (m, 2H, 3,5-H in C$_6$H$_4$$^t$Bu), 7.40-7.36 (m, 2H, 5-H in L$^1$ and 4-H in C$_6$H$_3$$^t$Bu$_2$), 7.31 (d, J=7.1 Hz, 1H, 5-H in L$^2$), 7.09 (dd, J=8.5 Hz, J=7.3 Hz, 1H, 6-H in L$^1$), 7.01-6.94 (m, 3H, 3-H in L$^2$, 3-H in L$^1$, 6-H in L$^2$), 2.68 (s, 3H, 7-Me in L$^2$), 2.45 (s, 3H, 2-Me in L$^2$), 2.24 (s, 3H, 2-Me in L$^1$), 1.38 (s, 3H, SiMeMe'), 1.35 (s, 9H, $^t$Bu in C$_6$H$_4$$^t$Bu), 1.32 (s, 18H, $^t$Bu in C$_6$H$_3$$^t$Bu$_2$), 1.29 (s, 3H, SiMeMe').
syn-Hafnocenes.
Anal. calc. for C$_{47}$H$_{56}$Cl$_2$HfSi: C, 62.83; H, 6.28. Found: C, 62.98; H, 6.44.
$^1$H NMR (CDCl$_3$): δ7.79 (d, J=8.7 Hz, 1H, 7-H in L$^1$), 7.51-7.49 (m, 2H, 2,6-H in C$_6$H$_4$$^t$Bu), 7.45-7.43 (m, 4H, 3,5-H in C$_6$H$_4$$^t$Bu and 2,6-H in C$_6$H$_3$$^t$Bu$_2$), 7.38 (s, 4-H in C$_6$H$_3$$^t$Bu$_2$), 7.16 (d, J=6.9 Hz, 1H, 5-H in L$^1$), 7.11 (d, J=6.9 Hz, 1H, 5-H in L$^2$), 6.88-6.86 (m, 2H, 3-H in L$^2$ and 6-H in L$^1$), 6.84 (s, 1H, 3-H in L$^1$), 6.77 (d, J=6.9 Hz, 1H, 6-H in L$^2$), 2.77 (s, 3H, 7-Me in L$^2$), 2.61 (s, 3H, 2-Me in L$^1$), 2.61 (s, 3H, 2-Me in L$^2$), 1.39 (s, 3H, SiMeMe'), 1.35 (s, 9H, $^t$Bu in C$_6$H$_4$$^t$Bu), 1.34 (s, 18H, $^t$Bu in C$_6$H$_3$$^t$Bu$_2$), 1.28 (s, 3H, SiMeMe').
b) Catalyst System Inventive Example 1

Anti-Complex 1-Hf was Used for Preparing Inventive Catalyst System ICS-1

Inside the glovebox, 97.85 mg of complex 1-Hf was mixed with 5 ml MAO in a septum bottle and the solution was stirred for 60 minutes and then 105.15 mg of tritylBF20 was added. The mixture was left to react overnight at room temperature inside the glovebox.

Inventive Example 2

Anti-Complex 2-Hf was Used for Preparing Inventive Catalyst System ICS-2

Inside the glovebox, 102.65 mg of complex 2-Hf was mixed with 5 ml MAO in a septum bottle and the solution was stirred for 60 minutes and then 105.15 mg of tritylBF20 was added. The mixture was left to react overnight at room temperature inside the glovebox.

Comparative Example 1

Anti-Complex 1-Zr was Used for Preparing Inventive Catalyst System CCS-1

Inside the glovebox, 88.03 mg of complex 1-Zr was mixed with 5 ml MAO in a septum bottle and the solution was stirred for 60 minutes and then 105.15 mg of tritylBF20 was added. The mixture was left to react overnight at room temperature inside the glovebox.

TABLE 1

| Catalyst System Composition | | | |
|---|---|---|---|
| cat. | Metallocene | Al/M[1] [mol/mol] | B/M[2] [mol/mol] |
| CE-1 | C1-Zr | 200 | 1.0 |
| IE-1 | C1-Hf | 200 | 1.0 |
| IE-2 | C2-Hf | 200 | 1.0 |

[1]Al/M molar ratio in catalyst, with M being Zr or Hf
[2]B/M molar ratio in catalyst, with M being Zr or Hf Polymerization In Examples IE-1, IE-1 and CE-1 the polymerization reaction were carried out in Parallel Polymerization Reactors (PPR) (provided by Symyx) (10 mL Reactor Volume) at 190° C.

Pre-Catalyst Preparation Procedure (Ternary System MC/MAO/tritylBF20):

Inside a glovebox, desired amount of metallocene was mixed with 5 ml MAO solution in a septum bottle and the solution was stirred for 60 minutes and then 105.15 mg of tritylBF20 was added. The mixture was left to react overnight at room temperature inside the glovebox. All catalysts were prepared according to the below recipe (Table 2).

TABLE 2 pre-catalyst preparation of the selected metallocenes.

| Example | CE-1 | IE-1 | IE-2 |
|---|---|---|---|
| C1-Zr [mg] | 88.03 | | |
| C1-Hf [mg] | | 97.85 | |
| C2-Hf [mg] | | | 102.65 |
| MAO [mg] | 1320 | 1320 | 1320 |
| TritylBF20 [mg] | 105.15 | 105.15 | 105.15 |
| Al/M[1] | 200 | 200 | 200 |
| B/M[2] | 1.0 | 1.0 | 1.0 |

MAO was used as 30% solution in toluene
[1]Al/M molar ratio in catalyst, with M being Zr or Hf
[2]B/M molar ratio in catalyst, with M being Zr or Hf Polymerization Procedure for PPR:

The selected catalysts were screened at 190° C., with polymerization solvent decane, at one MAO/M ratio (200), one B/M ratio (1.0) and 1-octene/ethylene ratios of 1 wt/wt ($C_8/C_2$=1.0 wt/wt). (M being Hf or Zr)

Stock solutions of the metallocenes and co-catalysts (MAO and Borate) were prepared to be used for each set of reactions.

The vessels were loaded inside a glovebox utilizing a 3-axis liquid handling robot. A pre-weighed glass vial with stirring paddles was sealed and purged with nitrogen. A volume of about 4 mL of corresponding solvent (decane) was filled in each PPR reactor. Then, adequate amount of triethyl aluminium (TEA) as scavenger was added, along with precise volume of octene as co-monomer at room temperature. The ethylene pressure was set to 10 bar to check any leaks. Then, the temperature and pressure had been increased to the set value (T=190° C. and 24 bar) and once the steady state was reached, the corresponding volume of pre-activated catalyst as a slurry in toluene had been injected in the reactor to start the polymerization under mechanical stirring. The run was quenched with $CO_2$ after the set amount of ethylene uptake had been reached (20 min as a maximum run time). The glass vials had been dried by vacuum centrifuge and weighed.

TABLE 3

PPR experiments conditions for ethylene/1-octene solution co-polymerization

| | CCS-1 | ICS-1 | ICS-2 |
|---|---|---|---|
| Catalyst system [µl] | 51.8 | 116.5 | 111.1 |
| Used 1-octene [g] | 0.45 | 0.45 | 0.45 |
| Decane [g] | 3.14 | 3.10 | 3.10 |
| TEAL Scavenger [µmol] | 15.0 | 15.0 | 15.0 |

TABLE 4

PPR experiments results for ethylene/1-octene solution co-polymerization

| Example | MC | Complex amount [mg] | Quench time [min] | 1-octene incorporation [wt % NMR] |
|---|---|---|---|---|
| CE-1 | Complex 1-Zr | 0.08 | 9.1 | 24.2 |
| IE-1 | Complex 1-Hf | 0.20 | 9.7 | 31.5 |
| IE-2 | Complex 2-Hf | 0.20 | 13.2 | 32.2 |

As can be seen from Table 4 the Hf-containing catalyst systems lead to clearly higher comonomer incorporation than the Zr-analogue.

The invention claimed is:
1. A catalyst system comprising:
(i) a metallocene complex of formula (I)

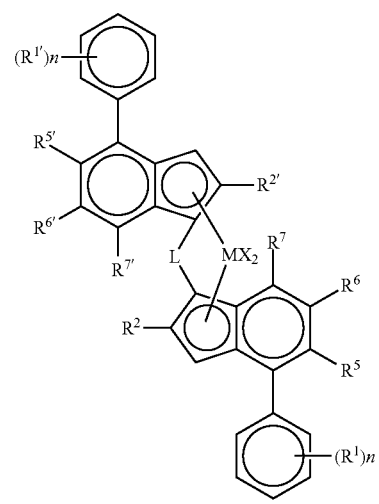

(I)

wherein
M is Hf;
each X is independently chlorine or a methyl radical;
L is a bridge of the formula —$SiR^8_2$—, wherein both $R^8$ are the same $C_1$-$C_{20}$-hydrocarbyl or $C_6$-$C_{10}$ aryl group;
n is 0, 1 or 2, with the proviso that n is not 0 for at least one of the phenyl groups;
$R^1$ and $R^{1'}$ are the same or are different and are a linear or branched $C_1$-$C_6$-alkyl group;
$R^2$ and $R^{2'}$ are the same or are different and are a $CH_2$—$R^9$ group, with $R^9$ being H or linear or branched $C_1$-$C_6$-alkyl group;
$R^5$ and $R^{5'}$ are the same or are different and are H or a linear or branched $C_1$-$C_6$-alkyl group or a OR group, wherein R is a $C_1$-$C_6$-alkyl group;
$R^6$ and $R^{6'}$ are the same or are different and are H or a $C(R^{10})_3$ group, with $R^{10}$ being the same or different and $R^{10}$ is H or a linear or branched $C_1$-$C_6$-alkyl group;
and
$R^7$ and $R^{7'}$ are the same or are different and are H or a linear or branched $C_1$-$C_6$-alkyl group;
(ii) an aluminoxane cocatalyst, wherein the aluminoxane cocatalyst is methyl aluminoxane; and (iii) a boron containing cocatalyst comprising an anion of the formula:

$$(Z)_4B^- \quad (III)$$

where Z is an optionally substituted phenyl derivative, said substituent being a halo-$C_{1-6}$-alkyl or halo group; and (iv) optionally an aluminum alkyl compound of formula (VIII) $AlR_3$, with R being a linear or branched $C_2$-$C_8$-alkyl group.

2. The catalyst system according to claim 1, wherein in the formula (I)
L is a bridge of the formula —$SiR^8_2$—, wherein both $R^8$ are the same $C_1$-$C_{10}$-hydrocarbyl or $C_6$-$C_{10}$-aryl group;
$R^1$ and $R^{1'}$ are the same and are a linear or branched $C_1$-$C_6$-alkyl group;
$R^2$ and $R^{2'}$ are the same and are a $CH_2$—$R^9$ group, with $R^9$ being H or linear or branched $C_1$-$C_4$-alkyl group;
$R^5$ and $R^{5'}$ are the same or are different and are H or a OR group, wherein R is a $C_1$-$C_4$-alkyl group;
$R^6$ and $R^{6'}$ are the same or are different and are H or a $C(R^{10})_3$ group, with $R^{10}$ being the same or different and $R^{10}$ is a linear or branched $C_1$-$C_4$-alkyl group;
$R^7$ and $R^{7'}$ are the same or are different and are H or a linear or branched $C_1$-$C_4$-alkyl group.

3. The catalyst system according to claim 1, wherein in the formula (I)
L is a bridge of the formula —$SiR^8_2$—, wherein both $R^8$ are the same $C_1$-$C_{10}$-hydrocarbyl or $C_6$-$C_{10}$-aryl group;
$R^1$ and $R^{1'}$ are the same and are a linear or branched $C_1$-$C_6$-alkyl group;
n is 0, 1 or 2, with the proviso that n is 1 for at least one of the phenyls groups;
$R^2$ and $R^{2'}$ are the same and are a $CH_2$—$R^9$ group, with $R^9$ being H or linear or branched $C_1$-$C_4$-alkyl group;
$R^5$ and $R^{5'}$ are the same or are different and are a H or a OR group, wherein R is a $C_1$-$C_4$-alkyl group;
$R^6$ and $R^{6'}$ are the same or are different and are H or a $C(R^{10})_3$ group, with $R^{10}$ being the same or different and $R^{10}$ is a linear or branched $C_1$-$C_4$-alkyl group;
whereby at least one of the ligands is unsubstituted in position 5 and 6; and
$R^7$ and $R^{7'}$ are the same or are different and are H or a linear or branched $C_1$-$C_4$-alkyl group.

4. The catalyst system according to claim 1, wherein the metallocene of formula (I) is selected from racemic dimethylsilyl[(2-methyl-4-phenyl-5-methoxy-6-tert-butylinden-1-yl)-(2-methyl-4-(4'-tertbutylphenyl)-inden-1-yl)] hafnium dichloride or dimethyl; and racemic dimethylsilyl[(2-methyl-4-(3',5'-di-tert-butylphenyl)-7-methylinden-1-yl)-(2-methyl-4-(4-tert-butylphenyl)-inden-1-yl)] hafnium dichloride or dimethyl, either in their syn or anti configuration.

5. A method of obtaining the catalyst system according to claim 1, comprising:
(a) forming a liquid/liquid emulsion system, said liquid/liquid emulsion system comprising a solution of the catalyst components (i) to (iii) dispersed in a solvent so as to form dispersed droplets;
(b) forming solid particles by solidifying said dispersed droplets; and
(c) optionally prepolymerizing the solid particles.

6. The catalyst system according to claim 1, being a non-supported catalyst system obtainable by contacting the metallocene of formula (I) as a solid or as a solution with the cocatalyst(s) previously dissolved in an aromatic solvent, or being obtainable by sequentially adding the catalyst components to the polymerization medium.

7. The catalyst system according to claim 1, wherein the catalyst system includes the aluminum alkyl compound.

8. A process for the preparation of an ethylene copolymer, comprising: polymerizing ethylene and a $C_{4-10}$-alpha-olefin comonomer in a solution process at a temperature greater than 100° C. in the presence of the catalyst system of claim 1.

9. The process according to claim 8, wherein the polymerization is performed
a) at a polymerization temperature of at least 110° C.,
b) a pressure in the range of 10 to 100 bar, and
c) in a liquid hydrocarbon solvent selected from the group of $C_{5-12}$-hydrocarbons, which is unsubstituted or substituted by $C_{1-4}$ alkyl group.

10. The process according to claim 8, wherein the ethylene copolymer has
a) a comonomer content (measured with NMR) up to 40 wt %;
b) a density (measured according to ISO 1183-187) of the in the range of 0.850 $g/cm^3$ to 0.950 $g/cm^3$;
c) a Mw/Mn value (measured with GPC) of less than 5; and
d) a melting point (measured with DSC according to ISO 11357-3:1999) below 130° C.

11. The catalyst system according to claim 1, wherein the boron containing cocatalyst is triphenylcarbeniumtetrakis (pentafluorophenyl) borate, N,N-dimethylcyclohexylammoniumtetrakis(pentafluorophenyl)borate, N,N-dimethylbenzylammoniumtetrakis(pentafluorophenyl)borate, or N,N-dimethylaniliniumtetrakis(pentafluorophenyl)borate.

12. The catalyst system according to claim 1, wherein in the formula (I) L is a bridge of the formula —$SiR^8_2$—, wherein both $R^8$ are a $C_1$-$C_4$-hydrocarbyl group.

13. The catalyst system according to claim 1, wherein in the formula (I) $R^2$ and $R^{2'}$ are both $CH_3$.

14. The catalyst system according to claim 1, wherein in the formula (I) $R^5$ and $R^{5'}$ are the same or are different and are H or a OR group, wherein R is a $C_1$-$C_4$-alkyl group.

15. The catalyst system according to claim 1, wherein in the formula (I) $R^6$ and $R^{6'}$ are the same or are different and are H or a $C(R^{10})_3$ group, with $R^{10}$ being the same or different and $R^{10}$ is H or a $C_1$-$C_2$-alkyl group.

16. The catalyst system according to claim 1, wherein in the formula (I) $R^7$ and $R^{7'}$ are the same or are different and are H or a $C_1$-$C_2$-alkyl group.

17. The catalyst system according to claim 1, wherein in the formula (I)
L is a bridge of the formula —$SiR^8_2$—, wherein both $R^8$ are a $C_1$-$C_4$-hydrocarbyl group; and
$R^2$ and $R^{2'}$ are both $CH_3$.

18. The catalyst system according to claim 1, wherein in the formula (I)
L is a bridge of the formula —$SiR^8_2$—, wherein both $R^8$ are a $C_1$-$C_4$-hydrocarbyl group;
$R^2$ and $R^{2'}$ are both $CH_3$;
$R^5$ and $R^{5'}$ are the same or are different and are H or a OR group, wherein R is a $C_1$-$C_4$-alkyl group;
$R^6$ and $R^{6'}$ are the same or are different and are H or a $C(R^{10})_3$ group, with $R^{10}$ being the same or different and $R^{10}$ is H or a $C_1$-$C_2$-alkyl group; and
$R^7$ and $R^{7'}$ are the same or are different and are H or a $C_1$-$C_2$-alkyl group.

\* \* \* \* \*